United States Patent
Aizawa et al.

(10) Patent No.: US 7,947,461 B2
(45) Date of Patent: May 24, 2011

(54) COLLOIDAL SILICA PARTICLE CONTAINING LIGHT-ABSORBING SUBSTANCE, NANO LIGHT-ABSORBING MATERIAL, ABSORPTION LABELING NANOBEAD KIT, AND METHOD FOR DETECTION OR QUANTIFICATION OF BIOLOGICAL MOLECULE USING THE COLLOIDAL SILICA PARTICLE CONTAINING LIGHT-ABSORBING SUBSTANCE

(75) Inventors: Hideki Aizawa, Tokyo (JP); Michio Ohkubo, Tokyo (JP)

(73) Assignee: The Furukawa Electric Co., Ltd., Tokyo (JP)

( * ) Notice: Subject to any disclaimer, the term of this patent is extended or adjusted under 35 U.S.C. 154(b) by 58 days.

(21) Appl. No.: 12/320,998

(22) Filed: Feb. 10, 2009

(65) Prior Publication Data
US 2009/0215096 A1 Aug. 27, 2009

Related U.S. Application Data

(63) Continuation of application No. PCT/JP2007/065662, filed on Aug. 9, 2007.

(30) Foreign Application Priority Data

Aug. 10, 2006 (JP) ................... 2006-218877
Aug. 10, 2006 (JP) ................... 2006-218903

(51) Int. Cl.
*G01N 33/53* (2006.01)
(52) U.S. Cl. ..................... 435/7.1; 435/7.2; 436/518
(58) Field of Classification Search ................. None
See application file for complete search history.

(56) References Cited

FOREIGN PATENT DOCUMENTS

| JP | 6-213891 A | 8/1994 |
|---|---|---|
| JP | 2003-262638 A | 9/2003 |
| JP | 2005-508493 A | 3/2005 |
| WO | WO-03/003015 A2 | 1/2003 |

OTHER PUBLICATIONS

Tarcha et al. Chapter 22, pp. 347-367 ACS Symposium Series, vol. 492.*
"Seikagaku Jiten", (the third edition); Tokyo Kagaku Dozin, p. 232; 1998.
S. Maeda et al., "Synthesis and Characterization of Carboxylic Acid-Functionalized Polypyrrole-Silca Microparticles", Macromolecules, vol. 28, No. 8, pp. 2905-2911; 1995.

* cited by examiner

*Primary Examiner* — Jacob Cheu
(74) *Attorney, Agent, or Firm* — Birch, Stewart, Kolasch & Birch, LLP

(57) ABSTRACT

A colloidal silica particle containing a light-absorbing substance, comprising a colloidal silica particle and a light-absorbing substance distributed over the colloidal silica particle, wherein the light-absorbing substance is chemically bound to or adsorbed on a silica component.

15 Claims, 2 Drawing Sheets

COLLOIDAL SILICA PARTICLE CONTAINING LIGHT-ABSORBING SUBSTANCE, NANO LIGHT-ABSORBING MATERIAL, ABSORPTION LABELING NANOBEAD KIT, AND METHOD FOR DETECTION OR QUANTIFICATION OF BIOLOGICAL MOLECULE USING THE COLLOIDAL SILICA PARTICLE CONTAINING LIGHT-ABSORBING SUBSTANCE

This application is a Continuation of copending PCT International Application No. PCT/JP2007/065662 filed on Aug. 9, 2007, which designated the United States, and on which priority is claimed under 35 U.S.C. §120. This application also claims priority under 35 U.S.C. §119(a) on Patent Application No(s). 2006-218877 and 2006-218903 filed in Japan on Aug. 10, 2006, the entire contents of which are hereby incorporated by reference into the present application.

TECHNICAL FIELD

The present invention relates to a colloidal silica particle containing a light-absorbing substance, a nano light-absorbing material, an absorption labeling nanobead kit, and a method for detection or quantification of a biological molecule using the colloidal silica particle containing the light-absorbing substance.

BACKGROUND ART

It is important to assay a quantity of a biological molecule, such as a protein or the like, not only for a fundamental research but also for a clinical diagnosis. For example, it is necessary and indispensable for an early diagnosis of a disease and an exact comprehension of a pathological condition to quantitate the quantity of the biological molecule, such as a cytokine, a hormone, a protein, a nucleic acid, or the like, that are included in body fluids, such as a plasma, a lymph, a tissue fluid, or the like, or to detect a specific biological molecule of very small quantity included in body fluids.

So far, an immunoanalytical technique (an immunoassay) is used for quantitating the above mentioned biological molecule, and it is able to provide as examples in principle a chemiluminescence method (a detection limit of $1.7 \times 10^{-18}$ to $1 \times 10^{-20}$ M), an enzyme-linked immunosorbent assay (ELISA) method (a detection limit of $1.7 \times 10^{-15}$ to $1 \times 10^{-18}$ M), a radioimunoassay (RIA) method (a detection limit of $1 \times 10^{-15}$ M), a fluorescence method (a detection limit of $1 \times 10^{-14}$ M), as technologies used for identifying an existence and a concentration of an analyte as an assay object in the immunoanalytical technique (the immunoassay) field. And, those are known as having a higher sensitivity in such the order (for example, refer to a nonpatent document 1).

Regarding the above mentioned ELISA method, an enzyme is used for a chromogenic reaction. Such the enzyme is not stable, and then there may be occurred a variation on a degree of chromophore due to a difference of enzyme activity between wells. Hence, sometimes it is not able to obtain data in high accuracy or in good reproductivity. Moreover, it takes time for a preparation of a substrate for an enzyme reaction or for a chromogenic reaction of the substrate by the enzyme reaction. And then long time period and complicated operations are required for obtaining an assay result. Hence, sometimes it is not able to process a large amount of specimen in a short time.

For resolving such the complication of the ELISA method, there is known the above mentioned fluorescence method using a reagent for labeling to be fluorescence labeled beforehand. Such the fluorescence method is convenient as the enzyme reaction is not included therein. However, the sensitivity is not sufficient, because a fluorescence intensity of a fluorescent molecule bound to one target substance is excessively small, because it occurs a self-quenching sometimes, and because a decoloration easily occurs regarding an organic dye to be used for labeling.

As the above mentioned immunoassay to detect or quantitate a biological molecule without using an enzyme reaction as well as the fluorescence method, an absorptiometric method is widely used for performing the detection and the quantitation of the biological molecule with a visual observation or by using such as an absorptiometer or the like, with binding a variety of light-absorbing substances to the biological molecule, such as a protein or the like, and with an absorption thereof as an indicator.

For such the light-absorbing substance, an organic molecule is mainly used. For example, an acrylamide gel after an electrophoresis is to be transcribed into a polyvinylidene difluoride (PVDF) film, it is stained using an Amido Black or a Coomassie Brilliant Blue (CBB) thereafter, and then an identification of a protein is to be performed by checking an absorption thereof with a visual observation. However, sometimes it is not able to perform the identification with a high reliability regarding a sample as a small quantity of not larger than one picomole by staining using the Amido Black or the CBB.

Regarding the immunoassay using the above mentioned absorptiometric method, a gold colloid immunoassay method is superior, that is for observing an absorption of a gold particle (for example, refer to patent document 1 and 2). However, the gold colloid is expensive and costly for such the gold colloid immunoassay method. Moreover, it is not able to use a variety of target particles using a difference of an absorption spectrum therebetween or a difference of an molar absorption coefficient therebetween, because an absorption wavelength is one type for a gold absorption, and because the molar absorption coefficient is constant as well. Hence, it is not able to apply it to an assay with a high throughput.

[Nonpatent Document 1] Kazutomo Imahori, Tamio Yamakawa, et al., "Seikagaku Jiten" the third edition (1998), P. 232, Tokyo Kagaku Dozin

[Patent Document 1] Japanese Patent Application Publication No. 2003-262638

[Patent Document 2] Japanese Patent Application Publication No. 1994-213891

DISCLOSURE OF THE INVENTION

A subject of the present invention is to provide a colloidal silica particle with enhancing an absorption coefficient ε by containing a light-absorbing substance with a high concentration, and a nano light-absorbing material comprised of the colloidal silica particle, as an absorption labeling nanobead for detecting or quantitating a biological molecule, such as a protein or the like, with a high sensitivity.

Moreover, a subject thereof is to provide a plurality of colloidal silica particles containing a light-absorbing substance to be a plurality of types thereof due to a difference of an absorption spectrum therebetween, and an absorption labeling nanobead kit comprising the colloidal silica particles to be a plurality of types as combined thereof, for being able to detect or quantitate a plurality of types of target biological molecules at the same time.

Further, a subject of the present invention is to provide a method for detection or quantification of a biological molecule using a nanobead for absorption labeling having a large molar absorption coefficient, as the method for detection or quantification of the biological molecule, such as a protein or the like, in a short time and with a high sensitivity, without performing an enzyme reaction.

Furthermore, a subject of the present invention is to provide a method for detection or quantification of a plurality types of target biological molecules at the same time, by using with combining plural number of colloidal silica particles containing a light-absorbing substance to be a plurality types thereof due to a difference of an absorption spectrum therebetween.

According to the present invention, it is able to provide the following techniques.

(1) A colloidal silica particle containing a light-absorbing substance, comprising: a colloidal silica particle; and a light-absorbing substance distributed over the colloidal silica particle, wherein the light-absorbing substance is chemically bound to or adsorbed on a silica component.

(2) The colloidal silica particle containing the light-absorbing substance according to (1), wherein a mean particle diameter is between 50 nm and 2000 nm.

(3) The colloidal silica particle containing the light-absorbing substance according to (2), wherein at least one type of the light-absorbing substance is distributed over the silica particle.

(4) The colloidal silica particle containing the light-absorbing substance according to (3), wherein an absorption maximum wavelength regarding an absorption spectrum of the colloidal silica particle is in a range of between 200 nm and 800 nm.

(5) The colloidal silica particle containing the light-absorbing substance according to (4), wherein a molar absorption coefficient of the colloidal silica particle regarding a maximal wavelength of the absorption spectrum is not less than $5 \times 10^7$ $M^{-1}$ $cm^{-1}$.

(6) The colloidal silica particle containing the light-absorbing substance according to (3), wherein a surface of the silica particle comprises an amino group, a hydroxyl group, a thiol group, a carboxyl group, a maleimide group, a cyano group, and/or a succinimidyl ester group.

(7) The colloidal silica particle containing the light-absorbing substance according to (3), wherein the surface of the silica particle is modified by using a substance specifically bound to or adsorbed on a target biological molecule.

(8) The colloidal silica particle containing the light-absorbing substance according to (3), wherein the target biological molecule is an antigen, an antibody, a DNA, an RNA, a saccharide, a sugar chain, a ligand, an acceptor, an avidin, a streptavidin, a biotin, a peptide, or a chemical substance.

(9) The colloidal silica particle containing the light-absorbing substance according to (3), wherein the colloidal silica particle is used for detecting or quantifying the target biological molecule, by absorption labeling as an absorption labeling nanobead for the target biological molecule, and by measuring an absorbance thereof, or by checking a chromophore thereof with a visual observation.

(10) The colloidal silica particle containing the light-absorbing substance according to (3), wherein the colloidal silica particles containing the light-absorbing substance individually contains one to four types of light-absorbing substances having a different maximal wavelength therebetween in the absorption spectrum respectively.

(11) A nano light-absorbing material comprised of the colloidal silica particle containing the light-absorbing substance according to (3).

(12) An absorption labeling nanobead kit comprising a set including at least two types of the colloidal silica particles containing the light-absorbing substance according to (3).

(13) The absorption labeling nanobead kit according to (12), wherein not less than two types of target biological molecules are detected or quantified at the same time.

(14) The absorption labeling nanobead kit according to (13), wherein not less than two types of the target biological molecules are detected or quantified at the same time, by absorption labeling specifically regarding not less than two types of the target biological molecules respectively, with using at least two types of the colloidal silica particles containing the light-absorbing substance.

(15) The absorption labeling nanobead kit according to (12), wherein at least two types of the colloidal silica particles containing the light-absorbing substance have a different absorption spectrum therebetween.

(16) The absorption labeling nanobead kit according to (12), wherein at least two types of the colloidal silica particles containing the light-absorbing substance individually contains one to four types of light-absorbing substances having a different maximal wavelength therebetween in the absorption spectrum respectively.

(17) A method for detection or quantification of a biological molecule wherein a target biological molecule in a specimen is modified by using a first recognition substance, comprising the steps of:

(a) performing a molecular recognition between a second recognition substance fixed on a plate and the target biological molecule;

(c) performing a molecular recognition of the first recognition substance using a colloidal silica particle containing a light-absorbing substance surface modified by using a third recognition substance; and (α) detecting or quantifying an absorption of the colloidal silica particle on the plate.

(18) A method for detection or quantification of a double antibody sandwich technique using a colloidal silica particle containing a light-absorbing substance, of which surface is modified by using an antibody for absorption labeling bound to an antibody recognition site of a target biological molecule.

(19) A method for detection or quantification of a biological molecule further comprising the steps of:

(a') absorption labeling a target biological molecule in a specimen using a colloidal silica particle containing a light-absorbing substance, and then performing a molecular recognition between a first recognition substance fixed on a plate and the target biological molecule absorption labeled by using the colloidal silica particle; and (α) detecting or quantifying an absorption of the colloidal silica particle on the plate.

(20) A method for detection or quantification of a biological molecule further comprising the steps of:

(a) performing a molecular recognition between a first recognition substance fixed on a plate and a target biological molecule in a specimen;

(b) performing a molecular recognition between a second recognition substance and the target biological molecule after molecular recognized with the first recognition substance;

(c) performing a molecular recognition of the second recognition substance by using a colloidal silica particle containing a light-absorbing substance surface modified by using a third recognition substance; and (α) detecting or quantifying an absorption of the colloidal silica particle on the plate.

(21) A method for detection or quantification of a biological molecule further comprising the steps of:

(a) performing a molecular recognition between a first recognition substance fixed on a plate and a target biological molecule in a specimen;

(b) performing a molecular recognition between a second recognition substance and the target biological molecule after molecular recognized with the first recognition substance;

(c') performing a molecular recognition of the second recognition substance using a third recognition substance;

(d) performing a molecular recognition of the third recognition substance using a light-absorbing colloidal silica particle surface modified by using a fourth recognition substance; and (α) detecting or quantifying an absorption of the colloidal silica particle on the plate.

(22) The method for detection or quantification of the biological molecule according to (17), wherein the target biological molecule is an antigen, an antibody, a DNA, an RNA, a saccharide, a sugar chain, a ligand, an acceptor, an avidin, a streptavidin, a biotin, a peptide, or a chemical substance.

(23) The method for detection or quantification of the biological molecule according to (18), wherein the target biological molecule is an antigen, an antibody, a DNA, an RNA, a saccharide, a sugar chain, a ligand, an acceptor, an avidin, a streptavidin, a biotin, a peptide, or a chemical substance.

(24) The method for detection or quantification of the biological molecule according to (17), wherein a mean particle diameter of the colloidal silica particles is between 50 nm and 2000 nm.

(25) The method for detection or quantification of the biological molecule according to (18), wherein a mean particle diameter of the colloidal silica particles is between 50 nm and 2000 nm.

(26) The method for detection or quantification of the biological molecule according to (17), wherein an absorption maximum wavelength regarding the absorption spectrum of the colloidal silica particle is in a range of between 200 nm and 800 nm.

(27) The method for detection or quantification of the biological molecule according to (18), wherein an absorption maximum wavelength regarding the absorption spectrum of the colloidal silica particle is in a range of between 200 nm and 800 nm.

(28) The method for detection or quantification of the biological molecule according to (26), wherein a molar absorption coefficient of a light-absorbing colloidal silica particle regarding an absorption maximal wavelength is not less than $5 \times 10^7$ $M^{-1}$ $cm^{-1}$.

(29) The method for detection or quantification of the biological molecule according to (27), wherein a molar absorption coefficient of a light-absorbing colloidal silica particle regarding an absorption maximal wavelength is not less than $5 \times 10^7$ $M^{-1}$ $cm^{-1}$.

(30) The method for detection or quantification of the biological molecule according to (17), wherein the colloidal silica particles containing the light-absorbing substance individually contains one to four types of light-absorbing substances having a different absorption maximal wavelength therebetween respectively.

(31) The method for detection or quantification of the biological molecule according to (18), wherein the colloidal silica particles containing the light-absorbing substance individually contains one to four types of light-absorbing substances having a different absorption maximal wavelength therebetween respectively.

(32) A method for detection or quantification of a biological molecule further comprising the steps of detecting or quantifying not less than two types of the target biological molecules at the same time, by absorption labeling specifically regarding not less than two types of the target biological molecules respectively, with using at least two types of colloidal silica particles containing a light-absorbing substance.

(33) The method for detection or quantification of the biological molecule according to the term (32), wherein not less than two types of target biological molecules are detected or quantified at the same time, by surface modifying at least two types of the colloidal silica particles containing the light-absorbing substance respectively, with a substance for specific molecular recognition regarding not less than two types of target biological molecules.

(34) The method for detection or quantification of the biological molecule according to (32), wherein the colloidal silica particle of at least two types of the colloidal silica particles containing the light-absorbing substance having a different absorption spectrum therebetween is surface modified by using a substance for specific molecular recognition regarding target biological molecules different therebetween, while, the colloidal silica particle having a similar absorption spectrum therebetween is surface modified by using a substance for specific molecular recognition regarding target biological molecules similar thereto.

(35) The method for detection or quantification of the biological molecule according to (34), wherein at least two types of the colloidal silica particles containing the light-absorbing substance have a different absorption spectrum therebetween.

And,

(36) The method for detection or quantification of the biological molecule according to (34), wherein at least two types of the colloidal silica particles containing the light-absorbing substance individually contains one to four types of light-absorbing substances having a different absorption maximal wavelength therebetween respectively;

are to be provided.

The above described and other aspects and advantages regarding the present invention will become to be clarified according to the following description with reference to the accompanying drawings properly.

BEST MODE FOR CARRYING OUT THE INVENTION

Figure 1:
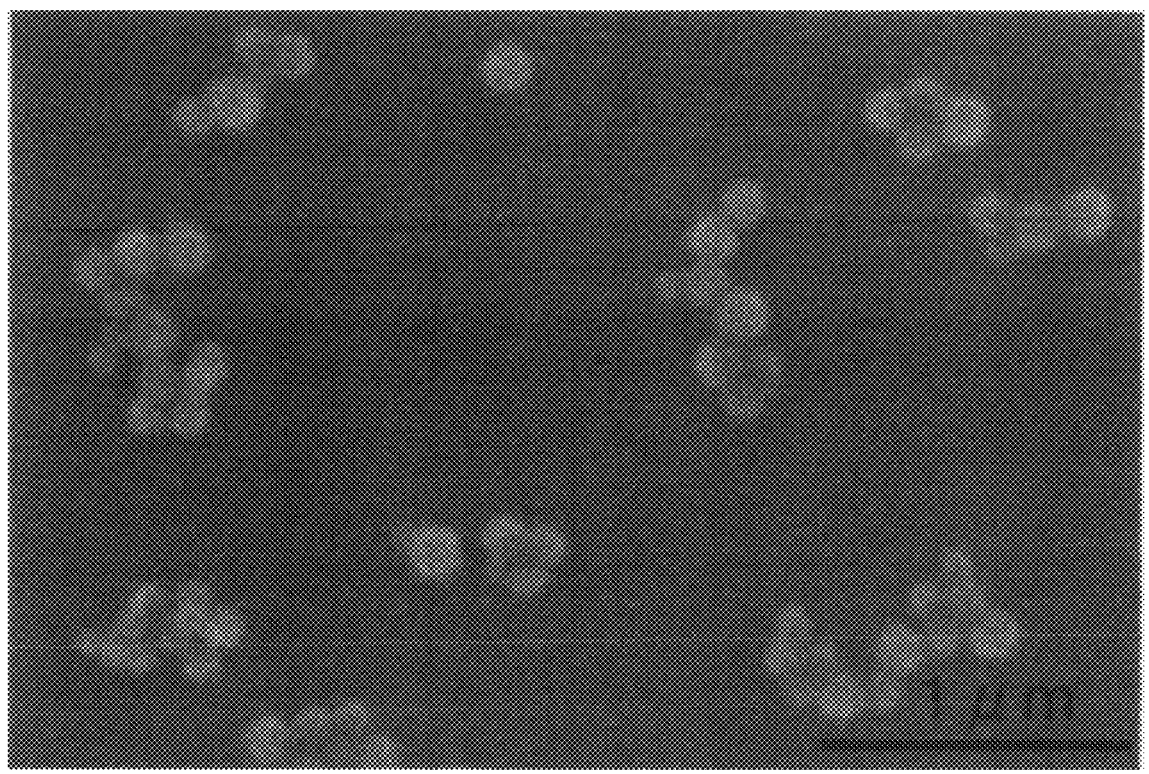
FIG. 1 is a view showing a SEM photo image of an obtained light-absorbing colloidal silica particle.

First, a colloidal silica particle containing a light-absorbing substance according to the present invention will be described in detail below. The colloidal silica particle containing the light-absorbing substance according to the present invention (simply referred to as a light-absorbing colloidal silica particle hereinafter as well) is an absorption labeling nanobead for absorption labeling a target biological molecule (including a physiologically active substance), wherein a light-absorbing substance is chemically bound to or adsorbed on a silica component.

The light-absorbing colloidal silica particle according to the present invention comprises a light-absorbing substance as it may be distributed over the colloidal silica particle from an inside of the above mentioned colloidal silica particle to a surface thereof, or the light-absorbing colloidal silica particle may comprise a core shell structure as a particle is covered with a silica component, wherein the light-absorbing substance is chemically bound to or adsorbed on the silica component. Here, an adsorption according to the present invention means a combine by a Van der Waals force or a hydrophobic interaction.

According to the colloidal silica particle containing the light-absorbing substance regarding the present invention, the light-absorbing substance is chemically bound to or adsorbed on the silica component and to be fixed therebetween. In such a case, it is desirable for a concentration of the light-absorbing substance corresponding to the light-absorbing colloidal silica particle to be not less than 20 mmol/l, and further preferable to be as between 40 mmol/l and 80 mmol/l.

Here, the concentration of the light-absorbing substance corresponding to the light-absorbing colloidal silica particle is to be the number of moles of the light-absorbing substance divided by a volume of the light-absorbing colloidal silica particle. The number of moles of the light-absorbing substance is to be evaluated from the absorbance of a light-absorbing silica particle dispersed colloid. Moreover, the volume of the light-absorbing colloidal silica particle is to be evaluated by the following steps of: collecting only the light-absorbing silica particles from a predetermined quantity (one ml for example) of the light-absorbing silica particle dispersed colloid; drying it; evaluating a mass thereof; and evaluating the volume thereof with assuming a density of the silica particle as 2.3 g/cm$^3$.

Here, an absorption according to the present invention means an absorption of a light to be measured as only a difference between an intensity $I_0$ of an incident light with an arbitrary wavelength and an intensity I of a transmitted light thereafter due to the light-absorbing colloidal silica particle or the light-absorbing substance.

Here, the transmitted light is a light after absorbed by the light-absorbing substance. On the contrary, a fluorescence is an emission with an intrinsic wavelength emitted by a fluorescent substance, that is, the absorption and the fluorescence are phenomena as different therebetween. Thus, regarding a measurement of the absorption and a measurement of the fluorescence, lights as measuring objects are different therebetween. Therefore, measurement systems, such as a measurement setup or the like, are different therebetween in a case of quantitating or detecting a target biological molecule.

Moreover, it is required to collect fluorescence at a light receiving unit regarding the above mentioned measurement of the fluorescence. Further, an exciting light and the fluorescence are to be separated, and then only the fluorescence is to be measured.

The present inventors found out the following facts. That is to say, in a case where a concentration of a fluorescent substance corresponding to silica particles is excessively high according to a colloidal silica particle containing a fluorescent substance, wherein the fluorescent substance is to be contained therein, sometimes a fluorescence intensity of the above mentioned colloidal silica particle containing the fluorescent substance becomes to be decreased due to a concentration quenching. On the contrary, according to a colloidal silica particle containing a light-absorbing substance, wherein the light-absorbing substance is to be contained in the silica particle, sometimes an absorbance of the above mentioned colloidal silica particle containing the light-absorbing substance becomes to be increased with increasing the concentration of the light-absorbing substance as higher corresponding to the silica particles.

Moreover, the present inventors applied the patent regarding a necessity for a mean particle diameter to be not larger than 30 nm for obtaining data in high reproducibility in the case of fluorescent labeling using the colloidal silica particle containing the fluorescent substance as the labeling nanobead for quantitating or detecting the target biological molecule (Japanese Patent Publication No. 2005-376401).

On the contrary, it is preferable for a light-absorbing colloidal silica particle according to the present invention to have a mean particle diameter of not less than 50 nm. In a case of less than 50 nm therefor, it is not able to have a molar absorption coefficient $\epsilon$ as sufficient for quantitating or detecting a target biological molecule, and then it is not able to apply it to a measuring apparatus, such as an absorptiometer, a plate reader, or the like.

Here, the absorbance (simply referred to as an A hereinafter as well) is expressed by the below described Lambert-Beer's equation:

$$A = \text{Log}_{10}(I_0/I)) = \epsilon bc = a_s bc',$$

[A: an absorbance, I: an intensity of a transmitted light, $I_0$: an intensity of an incident light, $\epsilon$: a molar absorption coefficient (M$^{-1}$ cm$^{-1}$), b: a light path length (cm), c: a concentration of a light-absorbing colloidal silica particle according to the present invention (M (mol/l)), $a_s$: a specific absorbance, and c': a concentration of the light-absorbing colloidal silica particle according to the present invention (g/l)].

The above mentioned concentration c' (g/l) is a value to be obtained by collecting only the light-absorbing colloidal silica particles from a predetermined quantity (one ml for example) of the light-absorbing colloidal silica particle dispersed liquid, and then by determining a mass to be obtained after drying it, as described above. While, the above mentioned concentration c (mol/l) is a value to be obtained by the following steps of: evaluating a size of a silica particle using a TEM photo; determining a volume regarding one particle; determining a mass regarding the one particle with assuming a density of the particle as 2.3 g/cm$^3$; collecting only the light-absorbing colloidal silica particles from a predetermined quantity (one ml for example) of the light-absorbing colloidal silica particle dispersed liquid; and determining the number of moles by using the mass of the silica particles to be obtained after drying it.

According to the present invention, a molar absorption coefficient $\epsilon$ of a light-absorbing colloidal silica particle means a molar absorption coefficient $\epsilon$ of a light-absorbing colloidal silica particle in a dispersed liquid, that is to be measured an absorbance thereof regarding the above mentioned light-absorbing colloidal silica particle dispersed liquid, and then to be obtained by applying it to the above mentioned Lambert-Beer's equation.

According to the colloidal silica particle containing the light-absorbing substance regarding the present invention, it is able to obtain the molar absorption coefficient $\epsilon$ thereof as not less than $5 \times 10^7$ (M$^{-1}$ cm$^{-1}$), as it is desirable for the $\epsilon$ to be as not less than $1 \times 10^8$ (M$^{-1}$ cm$^{-1}$), or it is preferable for the $\epsilon$ to be as between $2 \times 10^8$ (M$^{-1}$ cm$^{-1}$) and $1 \times 10^{13}$ (M$^{-1}$ cm$^{-1}$), and it is further preferable for the $\epsilon$ to be as between $1 \times 10^9$ (M$^{-1}$ cm$^{-1}$) and $1 \times 10^{13}$ (M$^{-1}$ cm$^{-1}$).

Regarding the absorbance, an absorption spectrum and the $\epsilon$ of the colloidal silica particle containing the light-absorbing substance according to the present invention, it is able to assay as a dispersed liquid, such as an aqueous dispersion, an ethanol dispersion, an N,N-dimethylformamide dispersion, or the like, with using an arbitrary absorptiometer or a plate reader.

Moreover, it is able to use the colloidal silica particle containing the light-absorbing substance according to the present invention as a nano light-absorbing material.

Further, the nano light-absorbing material according to the present invention is to be used as an absorption labeling nanobead for absorption labeling a target biological molecule, a chromophore particle for a immunoprecipitation method, or the like.

Still further, according to the present invention, it is also able to provide a nano light-absorbing material, wherein a plurality of, and further, plural types of the above mentioned colloidal silica particles containing the light-absorbing substance are to be used together therewith as an absorption labeling nanobead.

Still further, it is able to provide as examples for the above mentioned target biological molecule or the target physiologically active substance, any one of such as an antigen, an antibody, a DNA, an RNA, a saccharide, a sugar chain, a ligand, an acceptor, an avidin, a streptavidin, a biotin, a peptide, a chemical substance, or the like.

Still further, according to the present invention, the ligand means a substance to be specifically bound to a protein. For example, it means such as a substrate to be bound to an enzyme, a coenzyme, an adjustment factor, a hormone, a neurotransmitter, or the like, as including not only a molecule or an ion having a low molecular weight, but also including a substance having a high molecular weight.

Still further, the chemical substance is not limited to a natural organic compound, and it includes such as a compound to be synthesized artificially and having physiological activity, an environmental endocrine, or the like.

Furthermore, it is desirable for the light-absorbing colloidal silica particle according to the present invention to be a light-absorbing colloidal silica particle of which surface is modified by using a substance which is to be specifically bound to or adsorbed on the above mentioned target biological molecule required for quantitating and included in a specimen (for example, an arbitrary extract, a lysis solution, a medium and a culture, a solution, a buffer). And further preferably, it is to be a light-absorbing colloidal silica particle of which surface is modified by using a substance for molecular recognizing the above mentioned target biological molecule.

Next, a light-absorbing substance according to the present invention will be described in detail below.

The light-absorbing substance according to the present invention is to be chemically bound to or adsorbed on a silica component, and then to be formed as the above mentioned light-absorbing colloidal silica particle.

According to the present invention, the light-absorbing substance means a substance to absorb a light from a predetermined light source, such as a visible radiation, an ultraviolet radiation, a deep ultraviolet radiation, an infrared light, a far infrared, or the like. Moreover, it may have luminescent characteristics as well, such as a fluorescence or the like.

Moreover, there is no limitation in particular regarding the molar absorption coefficient ε the light-absorbing substance has, which is to be used for the present invention. However, it is desirable for the ε to be as not less than $1 \times 10^4$ ($M^{-1}$ $cm^{-1}$), and it is further preferable for the ε to be as between $5 \times 10^4$ ($M^{-1}$ $cm^{-1}$) and $8 \times 10^5$ ($M^{-1}$ $cm^{-1}$).

For the above mentioned light-absorbing substance, it is desirable to be as a substance to absorb a light from the above predetermined light source, and to be as being able to detect an absorption with using a detector for general purpose, such as a plate reader or the like, (for example, the Vmax™ (product name, produced by Molecular Devices Inc.), the microplate reader MPR-A4i (product name, produced by TOSOH CORPORATION)). In particular, it is desirable for the light-absorbing substance to be as an absorption maximum wavelength thereof in an absorption spectrum within a range of between 200 nm and 800 nm, and it is further preferable for the light-absorbing substance to be as the absorption maximum wavelength thereof in the absorption spectrum within a range of between 400 nm and 700 nm.

Here, in a case where a plurality of absorption peaks exist in an absorption spectrum, the absorption maximum wavelength means a wavelength with an absorbance as the maximum among that of the above mentioned absorption peaks.

As described above, it is desirable to use the light-absorbing substance of which the absorption maximum wavelength in the absorption spectrum exists within the range of between 200 nm and 800 nm. And more specifically for such an absorbent dye, it is desirable to use such as the DYQ-660, the DY-415, the DY-495, the DY-590, the DY-650 (all are the product names, produced by Dyomics GmbH), the Alexa Fluor™ 405, the Alexa Fluor™ 488, the Alexa Fluor™ 568, the Alexa Fluor™ 660, (all are the product names, produced by Invitrogen Corporation), or the like. Moreover, the DYQ-660, DY-590, the Alexa Fluor™ 405, the Alexa Fluor™ 660 are preferable among those, and in particular, it is further preferable to use the DYQ-660 and the Alexa Fluor™ 660.

(Chemical formula 1)

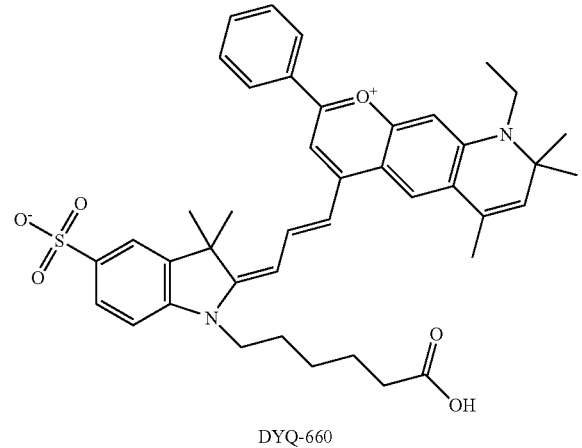

DYQ-660

(Chemical formula 2)

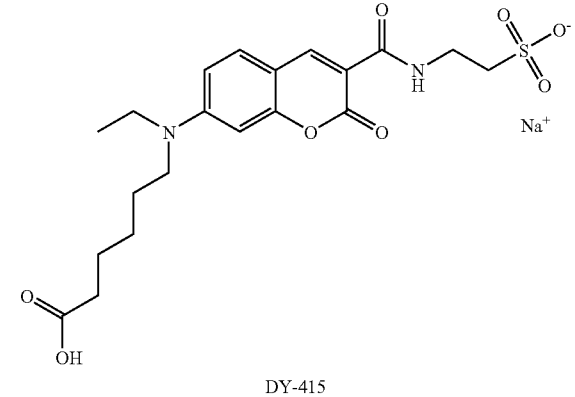

DY-415

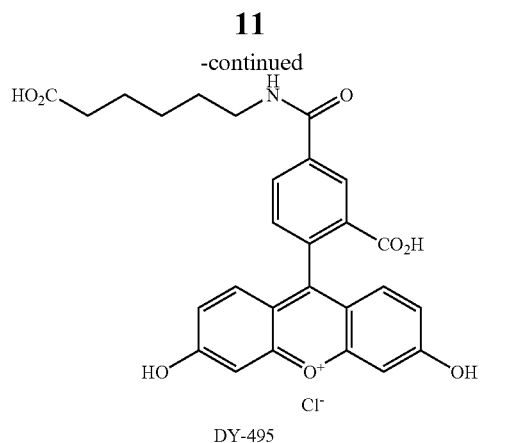

DY-495

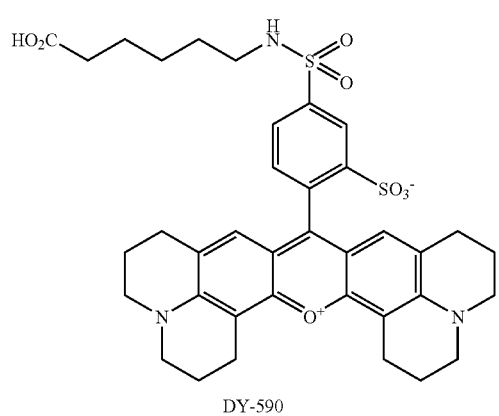

DY-590

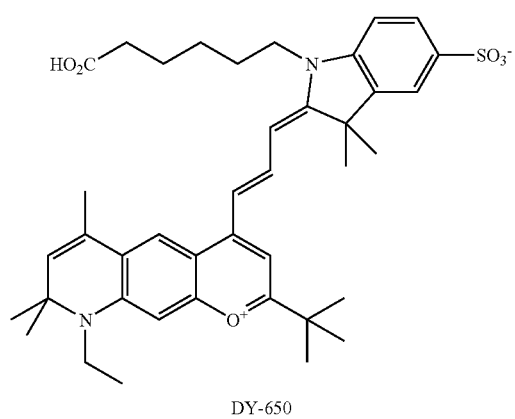

DY-650

(Chemical formula 3)

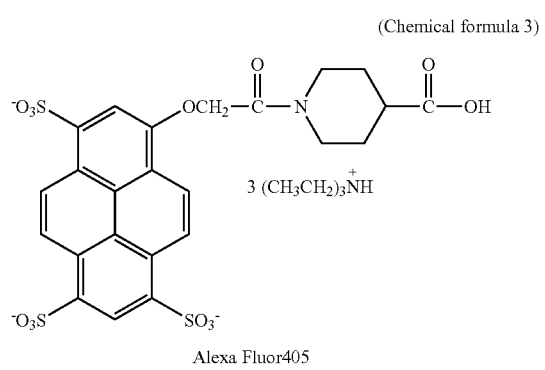

Alexa Fluor405

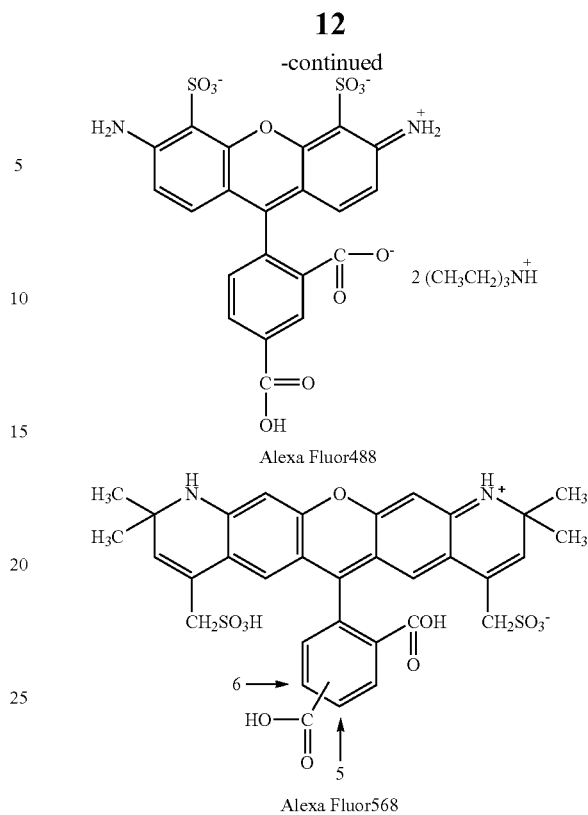

Alexa Fluor488

Alexa Fluor568

Next, a preparation of a colloidal silica particle containing a light-absorbing substance according to the present invention will be described in detail below.

Here, it is able to perform a preparation of the colloidal silica particle containing the light-absorbing substance according to the present invention, by reaction of the above mentioned light-absorbing substance with a silicon analogue, and then by polymerizing one type or not less than two types of the silicon analogues to a product obtained thereby as to be bound chemically thereto, such as a covalent bond, an ionic bond, or the like, or to be adsorbed thereon.

Regarding a method of the preparation of the colloidal silica particle containing the light-absorbing substance according to the present invention, it is desirable to perform the preparation by reaction of the above mentioned light-absorbing substance having an active group, such as an N-hydroxysuccinimido (NHS) ester group, a maleimide group, an isocyanate group, an isothiocyanato group, an aldehyde group, a paranitrophenyl group, a diethoxymethyl group, an epoxy group, a cyano group, or the like, with a silane coupling agent having a substituent to correspond to and react with such the active groups (for example, an amino group, a hydroxyl group and a thiol group), and then by polymerizing one type or not less than two types of the silicon analogues to a product obtained thereby as to be bound chemically thereto with a covalent bond.

Moreover, it is able to perform the preparation of the above mentioned colloidal silica particle containing the light-absorbing substance by performing the following processes (a) and (b):

(a) a process for forming a complex compound (3) of a light-absorbing substance/a silane coupling agent, by reaction of the light-absorbing substance (1) having an active ester group, such as an N-hydroxysuccinimido (NHS) ester or the like, with the silane coupling agent (2) having an amino group; and (b) a process for forming a colloidal silica particle containing the light-absorbing substance (5) by polymerizing the complex compound (3) of the light-absorbing substance/the silane coupling agent obtained at the above mentioned (a) to a silica chemical (4) under a condition of basicity.

The following is a reaction scheme regarding the above mentioned processes (a) and (b), as one example using the DYQ-660-NHS ester as the light-absorbing substance (1) having the active ester group, an aminopropyltriethoxysilane (APS) as the silane coupling agent (2) having the amino group, and a tetraethoxysilane (TEOS) as the silica chemical (4).

(Chemical formula 4)

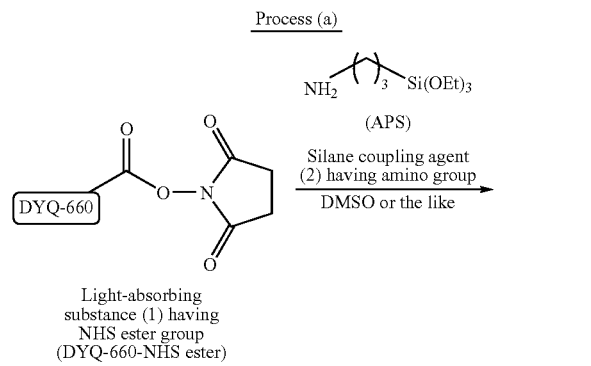

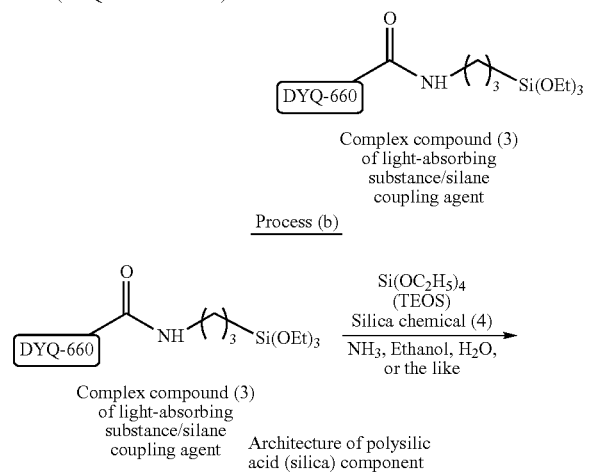

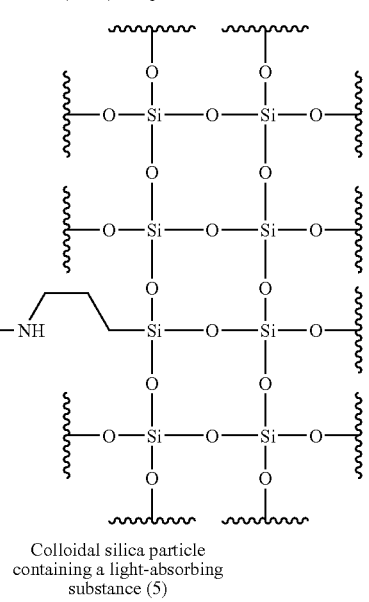

Here, it is able to perform a preparation of the light-absorbing substance (1) having the NHS ester group to be used at the above mentioned process (a), by esterification reaction of an arbitrary absorbent carboxylic compound with the N-hydroxysuccinimido. Moreover, it is possible to obtain a commercially available one as well.

For the above mentioned light-absorbing substance (1) having the NHS ester group, it is able to provide as examples, such as the DYQ-660-NHS ester, the DY-415-NHS ester, the DY-495-NHS ester, the DY-590-NHS ester, the DY-650-NHS ester (all are the product names, produced by Dyomics GmbH), the Alexa Fluor™ 405-NHS ester, the Alexa Fluor™ 488-NHS ester, the Alexa Fluor™ 568-NHS ester, the Alexa Fluor™ 660-NHS ester, (all are the product names, produced by Invitrogen Corporation), or the like. In particular, the DYQ-660-NHS ester or the Alexa Fluor™ 660-NHS ester are preferable among those.

(Chemical formula 5)

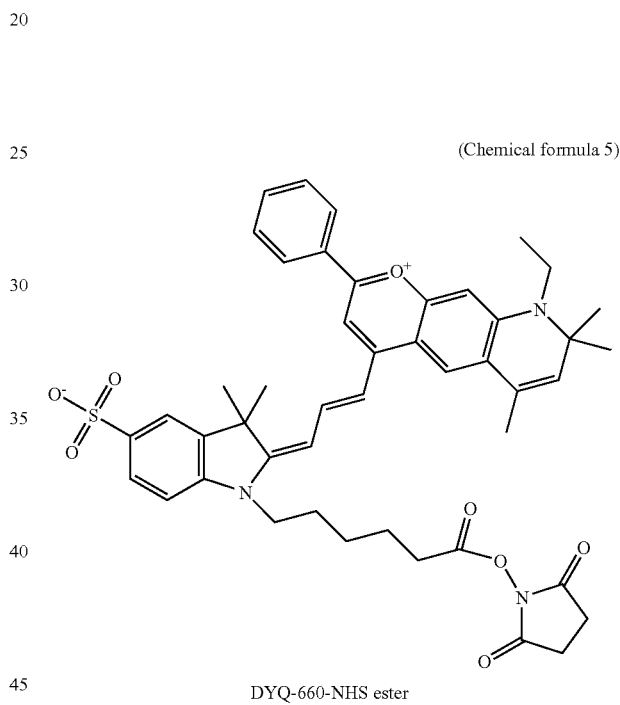

DYQ-660-NHS ester (Chemical formula 6)

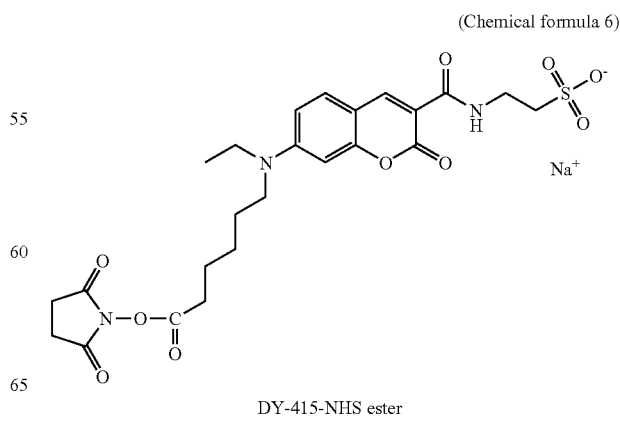

DY-415-NHS ester

-continued

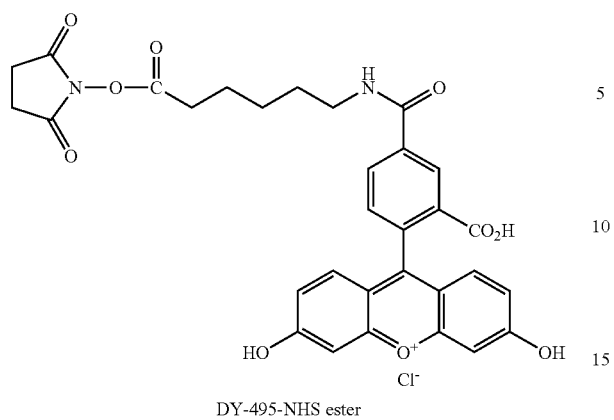

DY-495-NHS ester

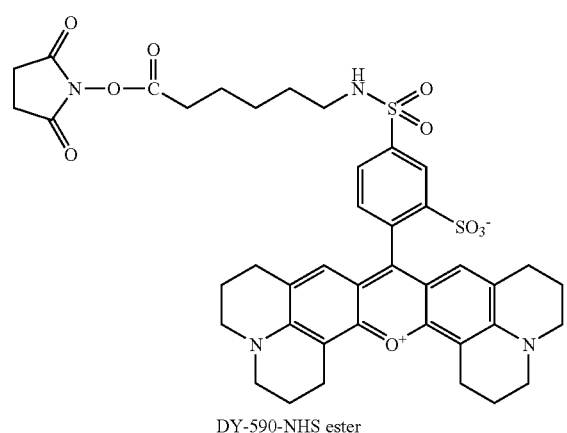

DY-590-NHS ester

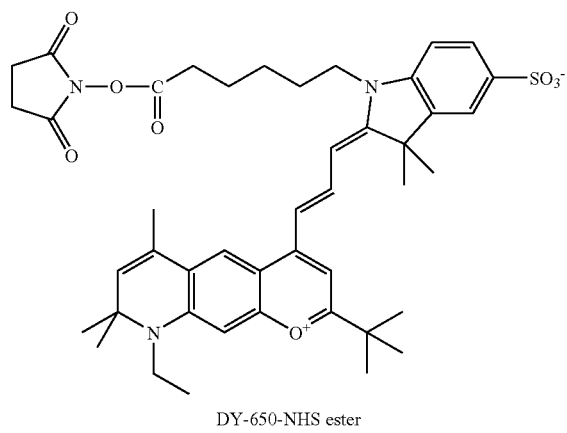

DY-650-NHS ester (Chemical formula 7)

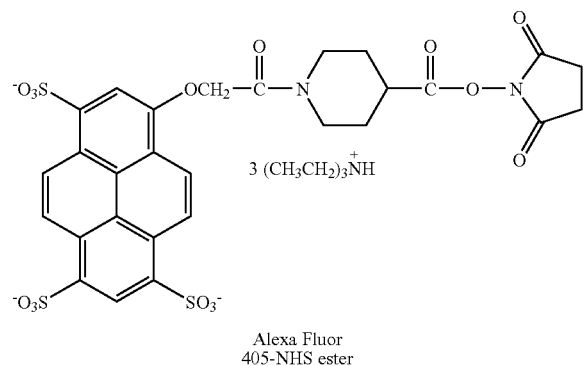

Alexa Fluor
405-NHS ester

-continued

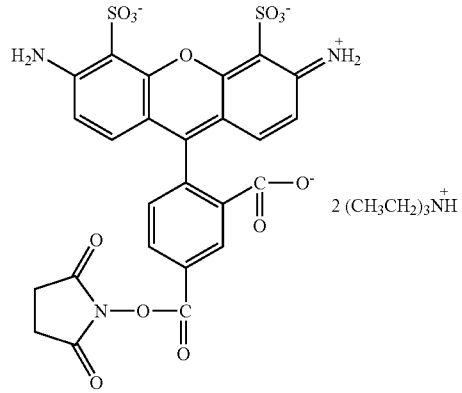

Alexa Fluor
488-NHS ester

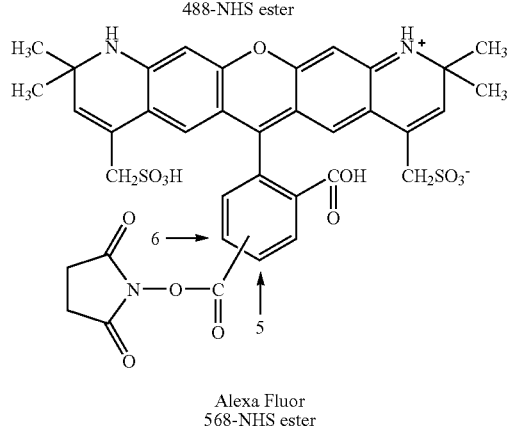

Alexa Fluor
568-NHS ester

Here, there is no limitation in particular regarding the above mentioned silane coupling agent (2) having the amino group. However, it is able to provide as examples therefor, such as a γ-aminopropyltriethoxysilane (APS), a 3-[2-(2-aminoethylamino)ethylamino]propyl-triethoxysilane, an N-2 (aminoethyl)-3-aminopropylmethyldimethoxysilane, a 3-aminopropyltriethoxysilane, or the like. And, it is preferable to use the APS among those.

Moreover, it is able to perform the reaction of the above mentioned light-absorbing substance (1) having the NHS ester group with the above mentioned silane coupling agent (2) having the amino group, by being soluble in a solvent, such as a dimethylsulfoxide (DMSO), an aqua, or the like, and then by reaction thereof with agitating under a condition of a room temperature (for example, 25° C.).

Further, there is no limitation in particular regarding a ratio between the above mentioned light-absorbing substance (1) having the NHS ester group and the silane coupling agent (2), that are to be used for the reaction. However, it is desirable to set as:

the light-absorbing substance (1) having the NHS ester group: the silane coupling agent (2) having the amino group =1:0.5 to 2 (mole ratio).

And it is further preferable to set as 1:0.8 to 1.2 (mole ratio).

Thus, a carbonyl group of the light-absorbing substance (1) and the amino group in the silane coupling agent (2) having the amino group become attached thereto in amide linkage (—NHCO—), and then it becomes able to obtain the complex compound (3) of the light-absorbing substance/the silane coupling agent. That is to say, in the above mentioned complex compound (3) of the light-absorbing substance/the silane coupling agent, the light-absorbing substance and a silica component become to be bound therebetween via the amide binding.

Next, at the process (b), the above mentioned complex compound (3) of the light-absorbing substance/the silane coupling agent is to be reacted with a silica chemical (4). Here, there is no limitation in particular regarding the silica chemical (4). However, it is able to provide as examples therefor, such as the tetraethoxysilane (TEOS), a γ-mercaptopropyltrimethoxysilane (MPS), a γ-mercaptopropyltriethoxysilane, a γ-aminopropyltriethoxysilane (APS), a 3-thiocyanatopropyltriethoxysilane, a 3-glycidyloxypropyltriethoxysilane, a 3-isocyanatopropyltriethoxysilane, the 3-[2-(2-aminoethylamino)ethylamino]propyl-triethoxysilane, or the like. And, it is desirable to use the TEOS, the MPS, or the APS among those. Moreover, it is preferable to use the TEOS in particular from a point of view of being able to architecture a polysilic acid component.

Here, there is no limitation in particular regarding a ratio between the complex compound (3) of the light-absorbing substance/the silane coupling agent and the silica chemical (4), however, it is desirable to set as between 50 and 40000 for a mole ratio of the silica chemical (4) corresponding to one mole of the complex compound (3) of the light-absorbing substance/the silane coupling agent, it is preferable to set it as between 100 and 2000, and it is further preferable to set it as between 150 and 1000.

Moreover, it is desirable to perform such the reaction under existences of an alcohol, an aqua and an ammonia. Here, it is able to provide a lower alcohol having the carbon number of 1 to 3, such as a methanol, an ethanol, a propanol, or the like, as an example for the alcohol.

Further, there is no limitation in particular regarding a ratio between the aqua and the alcohol according to such the reaction system, however, it is desirable to set an amount of the alcohol in a range of between 0.5 and 20 volume unit corresponding to one volume unit of the aqua, it is preferable to set it in a range of between 2 and 16 volume unit, and it is further preferable to set it in a range of between 4 and 10 volume unit. Still further, there is no limitation in particular regarding an amount of the ammonia as well, however, it is desirable to set a concentration of the ammonia as between 30 mM and 1000 mM, it is preferable to set it as between 60 mM and 500 mM, and it is further preferable to set it as between 80 mM and 200 mM.

Still further, it is able to perform such the reaction in a room temperature, and it is preferable to perform with agitating. And then by reaction thereof normally in several tens of minutes or in several tens of hours, it is able to perform the preparation of the colloidal silica particle containing the light-absorbing substance (5) according to the present invention.

Still further, it is able to perform the preparation of the colloidal silica particle containing the light-absorbing substance (5) according to the present invention as to be further uniform in particle size, or as preferably to be monodisperse, by performing the above mentioned process (b) in a reverse micellar solution.

Still further, there is no limitation in particular regarding a combination of an oil phase of the reverse micellar solution and a surface active agent, however, it is able to provide as examples, such as a heptane and an aerosol OT (AOT), an isooctane and the AOT, a mixed catalyst of a cyclohexane/a hexanol and the Triton™ X-100, or the like.

Still further, regarding a phase of minuscule droplet of water of the reverse micellar solution, a desirable concentration of the ammonia is similar to the above description regarding the above mentioned process (b). Still further, ditto regarding a quantitative ratio between the complex compound (3) of a dye silane coupling agent and the silica chemical (4), a desirable range thereof, or the like.

Still further, it is able to adjust properly a size (a diameter) of a silica particle to be performed a preparation by controlling such as the concentration of the silica chemical (4) to be used, a reaction time thereof, or the like, at the above mentioned process (b). That is to say, it is able to perform the preparation of a further smaller silica particle by reducing the concentration of the silica chemical (4) to be lower, or a reaction time thereof to be shorter (for example, refer to Blaaderenet, et al., "Synthesis and Characterization of Monodisperse Colloidal Organo-silica Spheres", J. Colloid and Interface Science 156, 1-18, 1993). On the contrary, it is able to perform the preparation of a further larger sized silica particle by performing the process (b) repeatedly a plurality times thereof. Thus, it is able to control at will the particle size (diameter) of the colloidal silica particle containing the light-absorbing substance to be obtained with a desirable size, such as from a nm order to a μm order. More specifically, it is possible to perform the preparation of the colloidal silica particle containing the light-absorbing substance having a minute size of such as several tens nm, or between 50 nm and 100 nm thereof in particular. Still further, it is also able to control to be a desirable particle size distribution therefor by performing processes thereafter. Thus, it becomes able to obtain the silica particles having a range within the desirable particle size distribution.

Furthermore, an assemblage of the colloidal silica particles containing the light-absorbing substance to be obtained by such a way may be purified with removing a coexistent ion and a coexistent impurity as required using a usual method of such as a ultrafiltration membrane or the like.

Thus, according to the preparation in such a way as described above, it becomes able to manufacture an assemblage of the silica particles having a spherical shape or a shape to be close to spherical. Here, it is able to define a minute particle having the shape to be close to spherical more specifically as having a ratio of a major axis and a minor axis as not larger than two.

Here, there is no limitation in particular regarding the mean particle diameter of the light-absorbing colloidal silica particle according to the present invention as far as it is able to detect by using an arbitrary detection method. However, it is desirable to be as between 50 nm and 2000 nm from a point of view of detection sensitivity, preferably to be as between 100 nm and 2000 nm, further preferably to be as between 200 nm and 2000 nm, and preferably in particular to be as between 200 nm and 400 nm.

Moreover, regarding the above mentioned particle diameter according to the present invention, an occupied area of the silica particles is evaluated using an image processing apparatus with a projected area in total of fifty pieces of the silica particles selected at random from an image of such as a transmission electron microscope (TEM), a scanning electron microscope (SEM), or the like, and then a mean value of a diameter (a mean circle equivalent diameter) is to be evaluated regarding a circle corresponding to a value as such the occupied area in total is divided by the number of the selected silica particles (fifty pieces).

Here, there is no limitation in particular regarding a coefficient of variation of the particle size distribution, that is to say, a CV value, however, it is desirable to be as not higher than 10%, and it is further preferable to be as not higher than 8%.

According to the present invention, a monodispersion means a particle assemblage having the CV value of not higher than 15%.

Moreover, it is able to achieve an ε value as higher than that of a free light-absorbing substance, and it becomes able to enhance a sensitivity, by fixing a light-absorbing substance in a silica particle inside, and then by making it containing thereof with a high concentration.

A preferable aspect (content light-absorbing substances, mean particle diameters, CV values, ε values and absorption maximum wavelengths) of the light-absorbing colloidal silica particle according to the present invention will be shown in Table 1 as below, however, the present invention is not limited thereto.

TABLE 1

| Content light-absorbing substance | Mean particle diameter (nm) | CV (%) | ε (M$^{-1}$cm$^{-1}$) | Absorption maximum wavelength (nm) |
|---|---|---|---|---|
| DYQ-660 | 58 | 11.8 | $1.1 \times 10^8$ | 660 |
| DYQ-660 | 169 | 8.5 | $2.6 \times 10^9$ | 660 |
| Alexa Fluor405 | 155 | 7.8 | $1.5 \times 10^9$ | 401 |
| Alexa Fluor405 | 556 | 7.3 | $6.9 \times 10^{10}$ | 401 |
| DY-590 | 122 | 8.4 | $4.1 \times 10^8$ | 580 |
| DY-590 | 725 | 9.1 | $1.6 \times 10^{11}$ | 580 |
| Alexa Fluor660 | 174 | 9.5 | $3.2 \times 10^9$ | 660 |
| Alexa Fluor660 | 1538 | 9.6 | $7.2 \times 10^{11}$ | 660 |

Next, a surface modification of a colloidal silica particle will be described in detail below.

It is known that generally a silica is chemically inactive, and it is easy to perform a modification thereof. Here, regarding the colloidal silica particle containing the light-absorbing substance according to the present invention, it is also possible to bind a desirable recognition molecule easily to a surface thereof, and it is able to modify the surface thereof to be mesoporous or smoothly shaped as well.

The light-absorbing colloidal silica particle according to the present invention is characterized in that it has a high hydrophilic property, and then it is easy to disperse it into a demineralized water or a buffer solution. Most of high polymer beads, such as a polystyrene or the like, has a hydrophobic property, and then it becomes required to perform a special treatment for dispersing it into the demineralized water or the buffer solution. On the contrary, it is not necessary for the above mentioned light-absorbing colloidal silica particle to perform such a special treatment.

Moreover, regarding the above mentioned light-absorbing colloidal silica particle, a light is less scattered by the silica because an extinction coefficient of the silica is small, and then it is able to absorb lights efficiently into the light-absorbing substance. Hence, it becomes able to realize a high molar absorption coefficient according to the light-absorbing colloidal silica particle. In a case of the high polymer beads, such as the polystyrene or the like, which contains the light-absorbing substance, the extinction coefficient of the high polymer beads, such as the polystyrene or the like, is relatively larger than that of the silica, and then scattering of lights occurs due to the high polymer beads, such as the polystyrene or the like. Hence, the absorption of light by using the light-absorbing substance becomes to be inefficient.

Regarding the surface modification of a colloidal silica particle according to the present invention, more specifically, it is able to form a light-absorbing colloidal silica particle having an acceptor group on a surface thereof to be able to bind to a desirable recognition molecule corresponding to the type of the silica chemical (4) to be used at the above mentioned process (b). For such the above mentioned acceptor group, it is able to provide as examples, such as the amino group, the hydroxyl group, the thiol group, the carboxyl group, the maleimide group, the succinimidyl ester group, or the like.

Here, a relation between the silica chemical (4) to be used for a reaction and an acceptor group to be formed on a surface of a light-absorbing colloidal silica particle to be obtained thereby will be shown in Table 2 as below.

TABLE 2

| Silica chemical (4) | Acceptor group formed on silica particle surface |
|---|---|
| Tetraethoxysilane | OH group |
| γ-Mercaptopropyltriethoxysilane | SH group |
| Aminopropyltriethoxysilane | NH$_2$ group |
| 3-Thiocyanato propyl triethoxysilane | SCN group |
| 3-Glycidyloxypropyltriethoxysilane | Epoxy group |
| 3-Isocyanato propyl triethoxysilane | CNO group |

Here, regarding the above obtained light-absorbing colloidal silica particle (5), in a case where an acceptor group is required to be introduced, which is different from the acceptor group to be introduced onto a surface thereof by the silica chemical (4) used for the reaction, it is able to achieve by processing further for the above mentioned light-absorbing colloidal silica particle (5) using a silica chemical different from the silica chemical (4) used at the process (b). It is able to perform such the treatment using the silica chemical different from the silica chemical (4) used at the process (b) by performing operations as similar to that of the above mentioned process (b).

Moreover, regarding the light-absorbing colloidal silica particle according to the present invention, it is able to modify the surface thereof by binding thereto or adsorbing thereon a desirable recognition molecule (for example, the antigen, the antibody, the DNA, the RNA, the saccharide, the sugar chain, the ligand, the acceptor, the avidin, the streptavidin, the biotin, the peptide, the chemical substance, or the like) corresponding to a type of the acceptor group to be comprised on the surface thereof.

Further, there is no limitation in particular regarding methods for modifying the surface of the colloidal silica particle containing the light-absorbing substance according to the present invention using a desirable recognition molecule, however, it is able to provide the following (i) to (iii) as examples.

(i) Regarding the light-absorbing colloidal silica particle having the thiol group to be performed the preparation using such as the MPS or the like, it is able to modify the surface thereof with a desirable recognition molecule via a disulfide bond, a thioester bond, or a binding via a thiol substitution reaction.

(ii) In a case where the above mentioned desirable recognition molecule has the amino group in particular, it is also able to bind the thiol group the light-absorbing colloidal silica particle has to the amino group the above mentioned desirable recognition molecule has, using a cross linking agent, such as a succinimidyl-trans-4-(N-maleimidylmethyl)cyclohexane-1-carboxylate (SMCC), an N-(6-maleimidecaproyloxy)succinimide (EMCS), or the like.

(iii) Regarding the light-absorbing colloidal silica particle having the amino group on the surface thereof which is performed the preparation using such as the APS or the like, it is able to bind such the amino group to the thiol group the desirable recognition molecule has, using the cross linking agent, such as the SMCC, the EMCS, or the like, as well as the above description. Moreover, it is also able to bind such the amino group to the amino group the desirable recognition molecule has, using a cross linking agent, such as a glutaraldehyde or the like. Further, it is able to modify the surface thereof using a desirable recognition molecule via the amide binding or a thiourea bond as well.

Still further, according to the present invention, the above mentioned light-absorbing colloidal silica particle may be modified directly using a target biological molecule, however, it is desirable to bind specifically to the target biological molecule, as the desirable molecule modifying the above mentioned light-absorbing colloidal silica particle (for example, the antibody, the DNA, the RNA, the sugar chain, the acceptor, the avidin, the streptavidin, the biotin, the peptide, or the like) itself further becomes an acceptor molecule, and then with using a specific molecular recognition reaction, such as an antigen-antibody reaction, a biotin-avidin reaction, a hybridization using a complementation of a base sequence, or the like.

Or, regarding the above mentioned light-absorbing colloidal silica particle, in a case where the above mentioned target biological molecule is modified by using a first molecular recognition substance, the surface thereof may be also modified by using a second substance for molecular recognizing the first molecular recognition substance.

Here, the molecular recognition reaction means a reaction derived from a specific interaction between biological molecules (including a physiologically active substance), such as (1) a hybridization between DNA molecules or between a DNA and an RNA molecules, (2) an antigen-antibody reaction, (3) a reaction between an enzyme (acceptor)-a substrate (ligand), or the like.

Next, an absorption labeling nanobead kit will be describe in detail below, which comprises a plurality types of light-absorbing colloidal silica particles as a set.

According to the present invention, in a case where different types of and a plurality of the above mentioned light-absorbing colloidal silica particle are used as one set for the below mentioned plate, it is able to detect or quantitate target biological molecules of not less than two types at the same time.

Moreover, the absorption labeling nanobead kit comprising a plurality types of the above mentioned light-absorbing colloidal silica particles as the set is comprised of a plurality types of the above mentioned light-absorbing colloidal silica particles wherein the above mentioned light-absorbing colloidal silica particles of not less than two types containing different light-absorbing substances are surface modified by using different surface modification substances.

Here, the above mentioned surface modification substance may be a substance to be bound specifically to or adsorbed on the above mentioned target biological molecule. Moreover, in a case where the above mentioned target biological molecule is modified by using a first molecular recognition substance, it may be a second substance for molecular recognizing the first molecular recognition substance as well.

As an example for the set of a plurality types of the above mentioned light-absorbing colloidal silica particles, it is able to provide a set, such as comprised of a colloidal silica particle containing the light-absorbing substance DYQ-660 surface modified by using a ligand for recognizing a target protein A and a colloidal silica particle containing the light-absorbing substance Alexa Fluor™ 405 surface modified by using a ligand for recognizing a target protein B, or the like. And then it is able to detect or quantitate the target protein A and the target protein B at the same time thereby.

According to the present invention, it is desirable to design the above mentioned light-absorbing colloidal silica particles of not less than two types to be as a plurality types with having a different absorption spectrum for every one piece of such the silica particles.

Moreover, regarding the above mentioned light-absorbing colloidal silica particles of not less than two types to be multiple, it is further preferable to design the absorption spectrum to be different from each other by containing one to four types of light-absorbing substances having different maximal wavelengths therebetween in the absorption spectrum for every one piece of such the silica particles.

As an example for the above mentioned light-absorbing colloidal silica particles of not less than two types, it is able to provide such as light-absorbing colloidal silica particles containing two types performed the preparation using the above mentioned method regarding the preparation of the light-absorbing colloidal silica particle according to the present invention for containing the Alexa Fluor™ 405 and the DYQ-660 as the two types of the light-absorbing substances for example, light-absorbing colloidal silica particles containing two types of the DY-415 and the Alexa Fluor™ 660, which is performed the preparation using the similar method, light-absorbing colloidal silica particles containing three types of the Alexa Fluor™ 568, the Alexa Fluor™ 405 and the DYQ-660, light-absorbing colloidal silica particles containing four types of the Alexa Fluor™ 488, the Alexa Fluor™ 568, the Alexa Fluor™ 405 and the DYQ-660, or the like.

Next, a method for detection or quantification of a target biological molecule according to the present invention (simply referred to as a method for detection or quantification of the present invention hereinafter as well) will be described in detail below.

Regarding the method for detection or quantification of the present invention, the above mentioned light-absorbing colloidal silica particle is to be used as a nanobead for absorption labeling a target biological molecule in a specimen (for example, an arbitrary extract, a lysis solution, a medium and a culture, a solution, a buffer).

According to the method for detection or quantification of the present invention, it is able to provide a target biological molecule (including the physiologically active substance) of such as the antigen, the antibody, the DNA, the RNA, the saccharide, the sugar chain, the ligand, the acceptor, the avidin, the streptavidin, the biotin, the peptide, the chemical substance, or the like, as an example as similar to the above description.

First, a case of absorption labeling directly a target biological molecule in a specimen by using the above mentioned light-absorbing colloidal silica particle regarding the method for detection or quantification of the present invention (simply referred to as a preferred aspect A regarding the method for detection or quantification of the present invention hereinafter) will be described in detail below.

It is preferable that the preferred aspect A regarding the method for detection or quantification of the present invention comprises the steps of:

(a') absorption labeling a target biological molecule in a specimen using a colloidal silica particle containing a light-absorbing substance, and then performing a molecular recognition between a first target biological molecule recognition molecule (simply referred to as a first recognition substance hereinafter) fixed on a plate and the target biological molecule absorption labeled by using the above mentioned colloidal silica particle; and (α) detecting or quantifying an absorption of the above mentioned colloidal silica particle on the plate.

Next, a case of molecular recognizing a target biological molecule using the above mentioned first recognition substance fixed on the plate, with a second target biological molecule recognition molecule (simply referred to as a second recognition substance hereinafter) which is different therefrom, and detecting or quantitating thereof will be described in detail below, regarding the method for detection or quantification of the present invention.

First, a case where the above mentioned light-absorbing colloidal silica particle is surface modified by using the above mentioned second recognition substance regarding the method for detection or quantification of the present invention (simply referred to as a preferred aspect B regarding the method for detection or quantification of the present invention hereinafter) will be described in detail below.

It is preferable that the preferred aspect B regarding the method for detection or quantification of the present invention comprises the steps of:

(a) performing a molecular recognition between a first recognition substance fixed on a plate and the above mentioned target biological molecule in the above mentioned specimen;

(b') performing a molecular recognition of the above mentioned target biological molecule after molecular recognized with the above mentioned first recognition substance, with using the above mentioned light-absorbing colloidal silica particle surface modified by using the above mentioned second recognition substance; and (α) detecting or quantifying an absorption of the above mentioned colloidal silica particle on the plate.

Moreover, it is further preferable for the preferred aspect B regarding the method for detection or quantification of the present invention to be a method for detection or quantification of a double antibody sandwich technique using the above mentioned light-absorbing colloidal silica particle surface modified by using an antibody for recognizing an antibody recognition site of a target biological molecule as an antibody for absorption labeling corresponding to the above mentioned second recognition substance.

As examples of the above mentioned method for detection or quantification of the double antibody sandwich technique according to the present invention, it is able to provide such as:

<i> a method for detection or quantification as the double antibody sandwich technique regarding a mouse immunoglobulin G type (IgG) as a target, by using an antimouse immunoglobulin antibody derived from a sheep as an antibody for fixing to a plate corresponding to the above mentioned first recognition substance, and by using a light-absorbing colloidal silica particle surface modified by using an anti-mouse immunoglobulin antibody derived from a goat as an antibody for labeling;

<ii> a method for detection or quantification as the double antibody sandwich technique regarding a human γ-interferon as a target, by using an antihuman γ-interferon antibody as an antibody for fixing to a plate corresponding to the above mentioned first recognition substance, and by using a light-absorbing colloidal silica particle surface modified by using an antihuman γ-interferon antibody as an antibody for labeling to be bound to an epitope different from the above mentioned antibody for fixing to the plate;

or the like.

Next, a case where the above mentioned light-absorbing colloidal silica particle is surface modified by using a third substance for molecular recognizing the above mentioned second recognition substance (simply referred to as a third recognition substance hereinafter) regarding the method for detection or quantification of the present invention (simply referred to as a preferred aspect C regarding the method for detection or quantification of the present invention hereinafter) will be described in detail below.

It is preferable that the preferred aspect C regarding the method for detection or quantification of the present invention comprises the steps of:

(a) performing a molecular recognition between a first recognition substance fixed on a plate and the above mentioned target biological molecule in the above mentioned specimen;

(b) performing a molecular recognition between the above mentioned second recognition substance and the above mentioned target biological molecule after molecular recognized with the above mentioned first recognition substance;

(c) performing a molecular recognition of the above mentioned second recognition substance using a light-absorbing colloidal silica particle surface modified by using the above mentioned third recognition substance; and (α) detecting or quantifying an absorption of the above mentioned colloidal silica particle on the plate.

As examples of the above mentioned second recognition substance according to the above mentioned aspect C, it is able to provide such as an arbitrary antibody (for example, the mouse IgG, a mouse IgM), an arbitrary antibody modified by using the biotin or the avidin, an arbitrary antibody modified by using a maltose binding protein, or the like.

Moreover, as examples of the light-absorbing colloidal silica particle surface modified by using the above mentioned third recognition substance corresponding thereto, it is able to provide such as a light-absorbing colloidal silica particle surface modified by using an arbitrary antibody binding protein (for example, the protein A, a protein G), a light-absorbing colloidal silica particle surface modified by using the biotin or the avidin, a light-absorbing colloidal silica particle surface modified by using an arbitrary sugar chain containing a maltose, or the like.

Next, a case where the above mentioned target biological molecule in the specimen is further modified by using the second recognition substance regarding the above described aspect C (simply referred to as a preferred aspect C' regarding the method for detection or quantification of the present invention hereinafter) will be described in detail below.

It is preferable that the preferred aspect C' regarding the method for detection or quantification of the present invention comprises the steps of:

(a) performing a molecular recognition between a first recognition substance fixed on a plate and a target biological molecule modified by using the above mentioned second recognition substance;

(c) performing a molecular recognition of the above mentioned second recognition substance using the above mentioned light-absorbing colloidal silica particle surface modified by using the above mentioned third recognition substance; and (α) detecting or quantifying an absorption of the above mentioned colloidal silica particle on the plate.

Moreover, as examples of the above mentioned target biological molecule modified by using the above mentioned second recognition substance according to the preferred aspect C' regarding the method for detection or quantification of the present invention, it is able to provide such as the DNA or the RNA modified by using the biotin or the avidin, the mouse IgG modified by using the biotin or the avidin, the mouse IgM modified by using the maltose binding protein, or the like.

Further, it is able to perform such the above mentioned method for modifying the above mentioned target biological molecule using the above mentioned second recognition substance, by using the method disclosed in such as Japanese Patent Application Publication No. 1997-154599, Japanese Patent Application Publication No. 2003-522158, or the like.

Still further, according to the preferred aspect C' regarding the method for detection or quantification of the present invention, as examples of the light-absorbing colloidal silica particle surface modified by using the above mentioned third recognition substance corresponding to such the second recognition substance, it is able to provide such as a light-absorbing colloidal silica particle surface modified by using the biotin or the avidin, a light-absorbing colloidal silica particle surface modified by using an arbitrary sugar chain containing a maltose, or the like.

Furthermore, according to the preferred aspect C' regarding the method for detection or quantification of the present invention, it is desirable for the combination of the above mentioned second recognition substance and the above mentioned third recognition substance to be any one selected from a group comprised of the below mentioned (i) to (ix) in particular:

(i) the above mentioned second recognition substance is to be an antigen, and the above mentioned third recognition substance is to be an antibody;

(ii) the above mentioned second recognition substance is to be an antibody, and the above mentioned third recognition substance is to be an antigen;

(iii) the above mentioned second recognition substance is to be a biotin, and the above mentioned third recognition substance is to be an avidin or a streptavidin;

(iv) the above mentioned second recognition substance is to be an avidin or a streptavidin, and the above mentioned third recognition substance is to be a biotin;

(v) the above mentioned second recognition substance is to be a saccharide or a sugar chain, and the above mentioned third recognition substance is to be a saccharide binding protein for binding specifically thereto;

(vi) the above mentioned second recognition substance is to be a saccharide binding protein, and the above mentioned third recognition substance is to be a saccharide or a sugar chain for binding specifically thereto;

(vii) the above mentioned second recognition substance is to be a ligand, and the above mentioned third recognition substance is to be an acceptor for binding specifically thereto;

(viii) the above mentioned second recognition substance is to be an acceptor, and the above mentioned third recognition substance is to be a ligand for binding specifically thereto; and (ix) the above mentioned second recognition substance is to be a chemical substance, and the above mentioned third recognition substance is to be an antibody or a peptide for binding specifically thereto.

Next, a case where the above mentioned light-absorbing colloidal silica particle is surface modified by using a fourth substance for molecular recognizing the above mentioned third recognition substance (simply referred to as a fourth recognition substance hereinafter) will be described in detail below (simply referred to as a preferred aspect D regarding the method for detection or quantification of the present invention hereinafter).

It is preferable that the preferred aspect D regarding the method for detection or quantification of the present invention comprises the steps of:

(a) performing a molecular recognition between a first recognition substance fixed on a plate and the above mentioned target biological molecule in the above mentioned specimen;

(b) performing a molecular recognition between the above mentioned second recognition substance and the above mentioned target biological molecule after molecular recognized with the above mentioned first recognition substance;

(c') performing a molecular recognition of the above mentioned second recognition substance by using the above mentioned third recognition substance;

(d) performing a molecular recognition of the above mentioned third recognition substance using a light-absorbing colloidal silica particle surface modified by using the above mentioned fourth recognition substance; and (α) detecting or quantifying an absorption of the above mentioned colloidal silica particle on the plate.

Moreover, according to the above mentioned aspect D, there is no limitation in particular regarding the above mentioned second recognition substance as far as it molecular recognizes the above mentioned target biological molecule, however, it is desirable to be an antibody of an arbitrary animal species.

Further, there is no limitation in particular regarding the above mentioned third recognition substance as far as it molecular recognizes the above mentioned second recognition substance. However, it is desirable to be a secondary antibody to be bound specifically to the above mentioned antibody as the above mentioned second recognition substance (for example, an antibody of an animal species (such as the goat or the like) different from an animal species (such as the mouse or the like) for a primary antibody). And, it is further preferable to be an arbitrary secondary antibody modified by using the biotin or the avidin, or an arbitrary secondary antibody modified by using the maltose binding protein.

Furthermore, as examples of the light-absorbing colloidal silica particle surface modified by using the above mentioned fourth recognition substance corresponding thereto, it is able to provide such as a light-absorbing colloidal silica particle surface modified by using an arbitrary antibody binding protein (for example, the protein A, the protein G), a light-absorbing colloidal silica particle surface modified by using the biotin or the avidin, a light-absorbing colloidal silica particle surface modified by using an arbitrary sugar chain containing a maltose, or the like.

Next, an aspect of detecting or quantitating a plurality types of target biological molecules at the same time regarding the method for detection or quantification of the present invention (simply referred to as a preferred aspect E regarding the method for detection or quantification of the present invention hereinafter) will be described in detail below.

According to the preferred aspect E regarding the method for detection or quantification of the present invention, it is able to detect or quantitate a plurality types of target biological molecules at the same time, by using with mixing a plurality types of light-absorbing colloidal silica particles having a different absorption spectrum from each other and to be bound specifically to a plurality types of target biological molecules respectively.

Moreover, according to the preferred aspect E regarding the method for detection or quantification of the present invention, a plurality types of the light-absorbing colloidal silica particles having the different absorption spectrum from each other are to be surface modified by using a substance for molecular recognizing specifically a different target biological molecule. While, light-absorbing colloidal silica particles having a similar absorption spectrum from each other are to be surface modified by using a substance for molecular recognizing specifically a similar target biological molecule.

It is preferable that the preferred aspect E regarding the method for detection or quantification of the present invention comprises the steps of:

(i) fixing a plurality types of target biological molecules onto a plate performed a treatment for fixing a target biological molecule;

(ii) preparing separately a plurality types of light-absorbing colloidal silica particles having a different absorption spectrum from each other, and performing a preparation of a plurality types of the light-absorbing colloidal silica particles to be bound to a molecular recognition substance corresponding to the above mentioned target biological molecule different from each other corresponding to each of the silica particles respectively;

(iii) absorption labeling individually and specifically a plurality types of target biological molecules to be fixed onto the plate by the above mentioned process (i), by using a plurality types of such the light-absorbing colloidal silica particles; and (α) detecting or quantifying individual absorptions of a plurality types of the above mentioned colloidal silica particles on the plate respectively.

As an example of the aspect E according to the present invention, it is able to provide a method for detection or quantification of a plurality types of target proteins comprising the steps of:

(i) adding a specimen containing a plurality types of target proteins to a plate performed a treatment for fixing a target protein, and fixing the proteins;

(ii) preparing separately a plurality types of light-absorbing colloidal silica particles having a different absorption spectrum from each other, and binding an antibody thereto for the different target protein corresponding to each of the silica particles respectively;

(iii) adding a plurality types of such the light-absorbing colloidal silica particles to a well wherein the target protein is to be fixed according to the above mentioned process (i), and absorption labeling the target protein; and (α) detecting or quantifying individual absorptions of the above mentioned colloidal silica particles on the plate respectively.

Thus, it becomes possible to detect or quantitate a plurality types of proteins from a similar well by measuring an absorbance for a plurality of wavelengths thereof.

According to the method for detection or quantification regarding the present invention, it becomes able to detect or quantitate a plurality types of biological molecules with a high efficiency from a sample of small quantity.

Moreover, regarding a measuring method for the above mentioned absorption or a measuring method for a chromophore of the above mentioned light-absorbing colloidal silica particle, it is able to provide such as a method wherein a light is irradiated onto a surface of a plate, and then a transmitted light thereof is to be measured, a method to measure a reflected light thereof, or the like. Further, regarding an equipment therefor, it is able to provide such as an arbitrary plate reader or the like. Still further, it is also able to apply a method for a quantitative analysis regarding an image on a surface of a plate detected by using a charge coupled device (CCD) camera, with using a computer.

Still further, according to the process for the quantification of the absorption of the above mentioned light-absorbing colloidal silica particle, a compensation of a measured value may be also performed by measuring an absorbance at wavelengths of not less than two.

Still further, a quantification of a target biological molecule is to be performed by forming a calibration curve according to a measurement of a control sample having a predetermined concentration, and then by comparing to such the calibration curve.

Still further, in a case of detecting a plurality types of target biological molecules in a specimen or evaluating an abundance ratio thereof, it is not required to form such a calibration curve therefor, and it is available to evaluate just a relative ratio of an absorption quantity.

Still further, according to the present invention, it is able to perform a molecular recognition reaction regarding the above mentioned individual processes by incubating under a constant reaction condition in an arbitrary buffer or a solvent, such as a phosphate buffered saline (PBS) or the like, and then by flushing out an unreacted substance, which is not to be performed the molecular recognition reaction, with using a cleaning solution.

Still further, there is no limitation in particular regarding the cleaning solution as far as it is able to remove efficiently the unreacted substance thereby without interfering in the molecular recognition reaction, and it is desirable to use such as the PBS containing a non-ionic surfactant, such as the Tween™ 20 or the like. Still further, regarding a method for cleaning, a plate may be soaked into the cleaning solution, or it may be also available to clean the plate with adding the cleaning solution from a top thereof.

Furthermore, regarding the light-absorbing colloidal silica particle to be used for the present invention, it is desirable to be a light-absorbing colloidal silica particle surface modified by using a substance to be specifically adsorbed on or bound to the above mentioned biological molecule to be contained in a specimen and required to be performed a quantification. And it is further preferable to be a light-absorbing colloidal silica particle surface modified by using a substance for molecular recognizing the above mentioned target biological molecule.

Next, a plate and a target biological molecule recognition molecule for plate fixing to be used for the method for detection or quantification regarding the present invention will be described in detail below.

Here, regarding the above mentioned light-absorbing colloidal silica particle, it is able to use preferably as a nanobead for absorption labeling for a various types of plates to be required a high-sensitive analysis, because it has a high molar absorption coefficient, and then because it is possible to check even for a small quantity with using the plate reader or a chromophore with a visual observation regarding the above mentioned light-absorbing colloidal silica particle.

Moreover, according to the present invention, it is desirable to fix on a plate a target biological molecule recognition molecule corresponding to a target biological molecule. In the case where a plurality types of the target biological molecules are to be assayed at the same time as described above, it is desirable to fix the target biological molecule recognition molecules to be able to recognize specifically the individual target biological molecules as the same number of the types of the target biological molecules. Such a target biological molecule recognition molecule is to be selected properly corresponding to a target biological molecule, and in a case where a target biological molecule recognition molecule is to be an antigen for example, it is able to use an antibody corresponding to such the antigen.

Further, there is no limitation in particular regarding the plate as far as it has a plurality of holes (wells) and has a plate shaped body to be able to fix a plurality of target biological molecule recognition molecules.

Still further, there is no limitation in particular on a shape, a size, a thickness, or the like, regarding such the plate. For example regarding the shape thereof, it is able to provide such as a rectangular shape, a polygonal shape, a circular shape, or the like. Regarding the size thereof, it is desirable to be in a range of between 80 $cm^2$ and 150 $cm^2$, and then it is able to be adjusted properly corresponding to a type or the like of a target biological molecule.

Still further, there is no limitation in particular regarding a substance for comprising the plate, and it is able to use such as a plastic, a glass, a quartz, a silicon, a ceramic, a metal, a rubber, or the like. It is preferable to use the plastic among those substances, and it is able to use for example, a polystyrene, a styrene-acrylonitrile copolymer, a polyethylene, a polypropylene, a polyvinyl chloride, a polymethyl methacrylate, a polyester, a polyamide, a polycarbonate, a cellulose acetate, or the like. And it is preferable in particular to use a plastic wherein the polystyrene is to be a principal component as it is able to perform a physical adsorption for a target biological molecule recognition molecule, such as an antibody or the like, thereto without being required a complicated operation. Still further, the plate may be a single plate shaped body comprised of a single substance, or may be a multilayered plate shaped body to be comprised by laminating a plurality types of substances. Still further, a surface of the plate may be performed a surface treatment properly corresponding to a type of a target biological molecule recognition molecule to be fixed thereon.

Still further, for fixing the target biological molecule recognition molecule onto the plate, it is able to use a method, such as a physical adsorption method, a covalent bond method, or the like. Still further, it is desirable to perform a treatment for a surface part of the plate beforehand on which a target biological molecule recognition molecule is to be fixed as fixing easily such the molecule corresponding to a type of the target biological molecule recognition molecule to be fixed thereon. Still further, it is desirable to perform a proper surface treatment for a surface part of the plate on which a target biological molecule recognition molecule is not to be fixed, for preventing from an unspecific adsorption of such as the target biological molecule or the like. For example, it is desirable to perform a blocking treatment using an arbitrary blocking drug comprised of a protein different from the target biological molecule, such as a fat-free milk, a serum albumin, a casein, or the like, for preventing from the unspecific adsorption of the target biological molecule, after fixing the target biological molecule recognition molecule onto such the plate.

Still further, it may be also available to use a commercial plate for the plate to be used for the present invention, such as the OptiPlate™ 96 (product name, produced by Perkin Elmer Inc.), the Falcon™ 96 (product name, produced by Becton, Dickinson and Company), the 96Well™ Glass Microplate (product name, produced by Nippon Sheet Glass Co., Ltd.), or the like.

Still further, according to the colloidal silica particle containing the light-absorbing substance regarding the present invention, it is suitable for an immunoassay of high sensitivity, because it has a high molar absorption coefficient due to containing the light-absorbing substance with a high concentration. And then for example, it becomes able to improve the detection sensitivity as ten to hundred times higher comparing to the ELISA method as the conventional absorption immunoassay.

Still further, according to the colloidal silica particle containing the light-absorbing substance regarding the present invention, it is not required to perform a complicated operation for modifying a surface thereof by using a preferred biological molecule with using a silane coupling agent. Thus, it becomes able to use for absorption labeling every possible biological molecule or physiologically active substance.

Still further, according to the colloidal silica particle containing the light-absorbing substance regarding the present invention, it is not required to perform a complicated operation in a case where it is to be used for an immunoassay, because it is not required to use an oxygen reaction. And then it is superior in accuracy and reproductivity regarding a measurement data because there is no problem occurring due to a variation on enzyme activity.

Still further, according to the colloidal silica particle containing the light-absorbing substance regarding the present invention, it is able to perform a preparation of a plurality types for the colloidal silica particles having a different absorption spectrum from each other, by changing the type of the light-absorbing substance to be contained therein.

Still further, it is possible to obtain a nano light-absorbing material according to the present invention with having a preferred particle diameter, and then it becomes superior in absorbance at a preferred wavelength. Therefor, it becomes able to use such the nano light-absorbing material as an absorption labeling nanobead for absorption labeling a target biological molecule, a chromophore particle for a immunoprecipitation method, or the like.

Still further, the absorption labeling nanobead kit according to the present invention comprises such a plurality types of the colloidal silica particles to be used at the same time, it is able to detect or quantitate a plurality types of biological molecules at the same time thereby, and it is effective for a case where there is limitation on an obtained sample, such as a clinical specimen or the like. Still further, it is useful for a case of such as quantitating a component of small quantity or the like, because it has a higher detection sensitivity comparing to that using the ELISA method.

Still further, it is able to use an equipment for detection as compact and cheaper comparing to that for a fluoroimmunoassay, because the detection or the quantification of the biological molecule is to be performed by measuring the absorbance.

Still further, according to the method for detection or quantification of a biological molecule regarding the present invention, it is able to perform a detection or a quantification of a biological molecule, such as a protein or the like, in a short time and with a high sensitivity, by using a colloidal silica particle containing a light-absorbing substance having a high molar absorption coefficient. And then for example, it becomes able to improve the detection sensitivity as ten to hundred times higher comparing to the ELISA method as the conventional absorption immunoassay.

Still further, according to the method for detection or quantification of a biological molecule regarding the present invention, it is not required to perform a complicated operation because it is not required to use an oxygen reaction. And then it is superior in accuracy and reproductivity regarding a measurement data because there is no problem occurring due to a variation on enzyme activity.

Still further, according to the method for detection or quantification of a biological molecule regarding the present invention, it is able to detect or quantitate a plurality types of biological molecules at the same time, by using colloidal silica particles containing a light-absorbing substance at the same time, that are to be a plurality types due to a difference of an absorption spectrum, and it is effective for a case where there is limitation on an obtained sample, such as a clinical specimen or the like. Furthermore, it is useful for a case of such as quantitating a component of small quantity or the like, because it has a higher detection sensitivity comparing to that using the ELISA method.

EXAMPLES

The present invention will be described in detail below, based on the examples. Here, the present invention is not limited to such the examples at all.

Example 1

A Method for Preparation of a Light-Absorbing Colloidal Silica Particle Antibody Modified on a Surface Thereof First, 3.3 mg of the DYQ-660-N-hydroxysuccinimido ester (produced by Dyomics GmbH) is to be dissolved in 1 ml of the dimethylsulfoxide (DMSO). Next, 1.0 µl of APS (3-aminopropyltriethoxysilane) is to be added thereinto, a reaction is to be performed for one hour at a room temperature (23° C.) thereafter, and then a complex solution of the DYQ-660/the silane coupling agent is to be obtained.

Next, 280 mg of the AOT (aerosol OT) is to be added into 4 ml of the heptane. Next, 40 µl of an aqua destillata and 40 µl of an aqueous ammonia (28%) are to be added thereinto, and then it is to be agitated very well. Thus, a reverse micellar solution is to be prepared.

Next, 40 µl of the complex solution of the DYQ-660/the silane coupling agent and 100 µl of the TEOS (tetraethyl orthosilicate) are to be added into the above mentioned reverse micellar solution, it is to be mixed very well at the room temperature, and then it is to be performed a reaction for 24 hours.

Next, 4 ml of an acetone is to be added thereinto, it is mixed very well thereafter. And then a centrifugal separation is to be performed for thirty minutes with a gravitational acceleration of 2200 g for removing a supernatant therefrom. Next, 1 ml of the ethanol is to be added to precipitated silica particles and to be dispersed, and then another centrifugal separation is to be performed for thirty minutes with a gravitational acceleration of 2200 g. Moreover, such the cleaning operation is to be repeatedly performed further two times. Next, 1 ml of the aqua destillata is to be added to precipitated silica particles and to be dispersed, and then another centrifugal separation is to be performed for thirty minutes with a gravitational acceleration of 2200 g. Further, such the cleaning operation is to be repeatedly performed further two times, and then an unreacted substance contained in the light-absorbing colloidal silica particle dispersion, such as the TEOS, the ammonia, or the like, is to be removed therefrom.

Thus, a colloidal silica particle containing the DYQ-660 is to be obtained with having a mean particle diameter of 138 nm. And a yield to be earned is approximately 44% therefor.

FIG. 1 is a view showing a SEM photo image of an obtained light-absorbing colloidal silica particle. The substance of spherical shape to be observed as white in the figure is the obtained light-absorbing colloidal silica particle. Thus, it is confirmed that the above mentioned light-absorbing colloidal silica particle is obtained by the observation of the SEM photo in FIG. 1.

(Measurements of absorption spectrum of colloidal silica particle containing DYQ-660 and molar absorption coefficient $\epsilon$ at absorption maximum wavelength)

Figure 2:
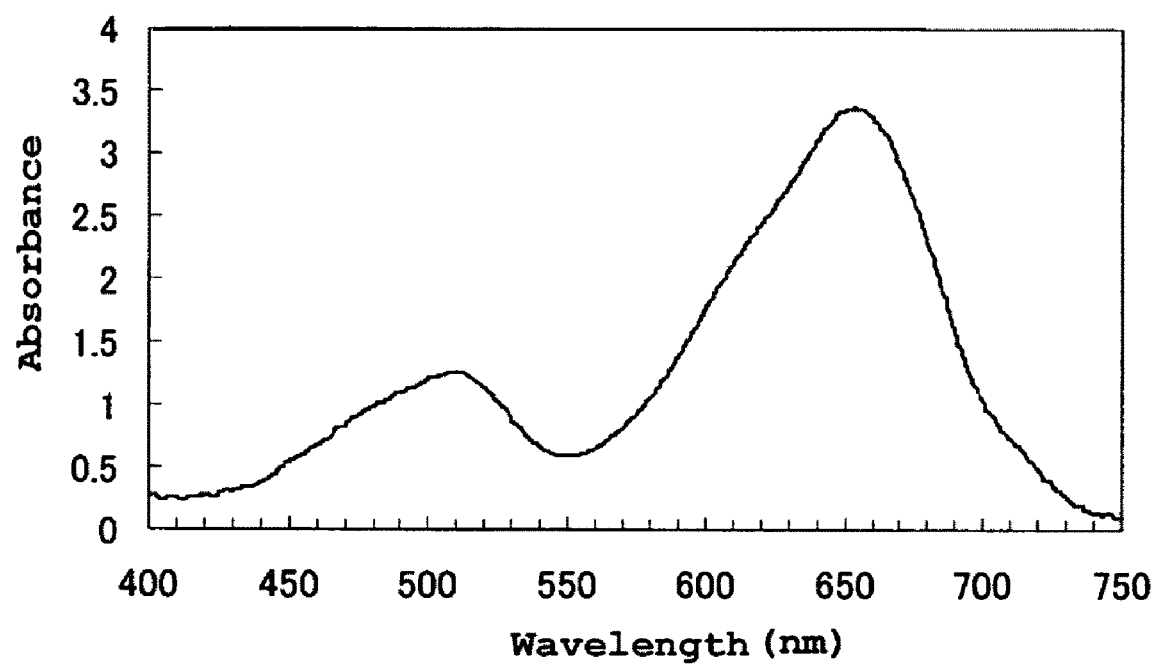
FIG. 2 is a graph showing an absorption spectrum of a colloidal silica particle containing the DYQ-660.

With using an absorptiometer (produced by Molecular Devices Inc.) and a cell with a light path length of 1 cm, the absorption spectrum of an aqueous dispersion (concentration: $1.37 \times 10^{-9}$ mol/l) of the colloidal silica particle containing the DYQ-660 and the molar absorption coefficient $\epsilon$ at the absorption maximum wavelength (660 nm) thereof are to be measured. FIG. 2 is a graph showing an absorption spectrum to be obtained. Moreover, the obtained $\epsilon$ at the wavelength of 660 nm is $2.4 \times 10^9$ $M^{-1}$ $cm^{-1}$.

(Surface Modification of Light-Absorbing Colloidal Silica Particle by Using Antibody)

First, the silica particle containing the DYQ-660 is to be dispersed into 1 ml of the phosphate buffered saline (PBS). Next, 400 µl of a compound of a 3-sulfo-N-hydroxysuccinimido (Sulfo-NHS) and an 1-ethyl-3(3-dimethylaminopropyl)-carbodiimide (EDC) (0.05 M Sulfo-NHS, 0.2 M EDC, dissolved in the PBS) is to be added into 50 µl of the silica particle dispersion containing the DYQ-660, and then it is to be mixed for ten minutes. Moreover, 50 µl of an antimouse immunoglobulin antibody 100 µg/ml derived from a goat (produced by LAB VISION Co.) is to be added thereinto, and then it is to be mixed for further one hour.

Next, light-absorbing colloidal silica particles are to be precipitated by performing a centrifugal separation for removing a supernatant therefrom, and then an unreacted reagent is to be removed by performing a dialysis two times for the PBS. Thus, it becomes able to obtain the light-absorbing colloidal silica particle of which surface is modified by using the antimouse immunoglobulin antibody derived from the goat.

Example 2

Determination of Immunoglobulin Protein Concentration in Hybridoma Culture Supernatant First, 10 µl of an antimouse IgG antibody derived from a sheep (produced by LAB VISION Co.) is to be added into 10 ml of the PBS, for fixing the antibody to a plate, and it is to be aggregate lightly for performing a preparation of a sheep antibody solution for plate fixing.

Next, the sheep antibody solution for plate fixing is to be moved to a reservoir, and then 100 µl thereof is to be added to every one well of the 96 well plate (the Falcon™ 96 (product name, produced by Becton, Dickinson and Company) using the PIPETMAN™ of eight-barreled type.

Next, it is to be incubated for one to two hours at 37° C., and then the above mentioned antimouse IgG antibody derived from the sheep is to be fixed in the individual wells of the above mentioned plate.

Next, 1.5 g of the fat-free milk is to be dissolved in 30 ml of the PBS, for blocking. And then 15 ml of the obtained solution is to be moved to a reservoir different from the above mentioned one, and then 150 µl thereof is to be added to every one well of the 96 well plate using the PIPETMAN™ of eight-barreled type.

Next, it is to be incubated for one to two hours at 37° C., for blocking. And then using nine of 1.5 ml Eppendorf tubes, every 450 µl of the PBS solution containing 5% fat-free milk is to be put thereinto respectively, for preparing a 5% fat-free milk solution.

Next, a culture supernatant and a culture solution of a hybridoma cellula (produced by Takara Bio Inc.) are to be prepared, which secretes an immunoglobulin (a mouse IgG) as a target.

Next, each 50 ml of the above mentioned culture supernatant and the culture solution is to be diluted by 1/10, 1/100 and 1/1000 respectively.

Next, a preparation is to be performed for a correlation sample (200 ng/ml of the immunoglobulin (mouse IgG)).

After removing the solution from the plate finished the above mentioned blocking, the above mentioned plate is to be rinsed four times using the PBS solution containing 0.1% Tween™ 20. And then the above mentioned plate is to be swished water off with enswathing using a tissue paper.

Next, the above mentioned 5% fat-free milk solution is to be put into all of the wells of the above mentioned plate with 100 µl for every one well respectively.

Next, the correlation sample, the culture supernatant of the hybridoma cellula and the culture solution thereof, that are performed the preparation as described above, are to be added to a top of individual columns respectively, and then a double dilution is to be repeated. Moreover, it is to be incubated for one to two hours at 37° C., and then the target mouse IgG is to be fixed on the plate.

Next, for absorption labeling, the above mentioned light-absorbing colloidal silica particle surface modified by using 200 µl of the above obtained antimouse immunoglobulin antibody derived from the goat (concentration: 20 µM, solvent: PBS) is to be added to 10 ml of the PBS.

After removing the solution from the plate finished fixing the target mouse IgG in a same way as described above, it is to be rinsed four times using the 0.1% Tween™ 20/PBS solution. And then the above mentioned plate is to be swished water off with enswathing using a tissue paper.

Next, the above mentioned light-absorbing silica particle colloidal liquid is to be put into such the plate with 100 µl for each.

Next, the target mouse IgG is to be absorption labeled using the above mentioned light-absorbing silica colloidal particle, by incubating for one hour at 37° C.

Next, the above mentioned plate is to be rinsed four times using the 0.1% Tween™ 20/PBS solution.

Next, 500 µl of the solvent PBS is to be added to individual wells, and then an absorbance at a wavelength of 650 nm is to be measured using the plate reader Vmax™ (product name, produced by Molecular Devices Inc.).

Next, a calibration curve is to be formed using a correlation sample having a predetermined concentration.

Thus, a concentration is to be calculated regarding the immunoglobulin (mouse IgG) in the above mentioned culture supernatant of the hybridoma.

INDUSTRIAL APPLICABILITY

According to the colloidal silica particle containing the light-absorbing substance regarding the present invention, it is able to enhance the molar absorption coefficient $\epsilon$ by containing the light-absorbing substance with a high concentration, it becomes possible to perform a high-sensitive detection. Moreover, it becomes able to surface modify for targeting a predetermined biological molecule without requiring a complicated operation therefor, and then it becomes available to be a preferred particle diameter thereof.

Further, according to the colloidal silica particle containing the light-absorbing substance regarding the present invention, it is able to be a plurality types thereof by containing a plurality of different light-absorbing substances, and then it is able to be a particle having a plurality of local maximums in an absorption spectrum by containing a plurality types of light-absorbing substances having a different maximal wavelength from each other in the absorption spectrum. Thus, it becomes available to be a so-called bar code absorption labeling nanobead.

Still further, it is available to use a combination of plural numbers of the above mentioned colloidal silica particle containing the light-absorbing substance to be a plurality types thereof as the bar code absorption labeling nanobead kit to be able to detect or quantitate a plurality types of target biological molecules at the same time.

Still further, according to the method for detection or quantification of the biological molecule regarding the present invention, it is able to surface modify for targeting a predetermined biological molecule without requiring a complicated operation. And also it is available to use for a high-sensitive detection and quantification of a biological molecule, by using a colloidal silica particle to be able to have a preferred particle diameter, by containing a light-absorbing substance as a high concentration, and by forming it to be a nanobead for absorption labeling to be able to enhance the molar absorption coefficient $\epsilon$.

Still further, according to the method for detection or quantification of the biological molecule regarding the present invention, it is able to form the above mentioned colloidal silica particle containing the light-absorbing substance to be a plurality types thereof by containing different light-absorbing substances. And then it is able to be a particle having a plurality of absorption local maximums by containing a plurality types of light-absorbing substances having a different absorption maximal wavelength from each other. Furthermore, it is available to use a combination of plural numbers of the above mentioned colloidal silica particle containing the light-absorbing substance to be a plurality types thereof for being able to detect or quantitate a plurality types of target biological molecules at the same time.

Thus, the present invention is described with the embodiments thereof, however, the present invention will not be limited to every detail of the description as far as a particular designation, and it should be interpreted widely without departing from the spirit and scope of the present invention as disclosed in the attached claims.

The present invention claims the priority based on Japanese Patent Application No. 2006-218877 patent applied in Japan on the tenth of Aug., 2006, and on Japanese Patent Application No. 2006-218903 patent applied in Japan on the tenth of Aug., 2006, the entire contents of which are expressly incorporated herein by reference.

What is claimed is:

1. A method for detection or quantification of a biological molecule wherein a target biological molecule in a specimen has a first recognition substance, attached thereto comprising the steps of:
    (a) performing a molecular recognition between a second recognition substance fixed on a plate and the target biological molecule;
    (b) performing a molecular recognition of the first recognition substance using a colloidal silica particle containing at least one kind of light absorbing member selected from the group consisting of DY590, DY495, DY415, Alexa Fluor405, Alexa Fluor488 and Alexa Fluor568 having a third recognition substance attached to a surface thereof; and
    (c) detecting or quantifying an absorption of the colloidal silica particle on the plate.

2. A method for detection or quantification of a target biological molecule in a double antibody sandwich technique, comprising the step of:
   detecting or quantifying absorbance by a colloidal silica particle containing at least one kind of light absorbing member selected from the group consisting of DY590, DY495, DY415, Alexa Fluor405, Alexa Fluor488 and Alexa Fluor568, wherein the surface of the particle has an antibody attached thereto, wherein said antibody binds to an antibody recognition site of the target biological molecule.

3. A method for detection or quantification of a biological molecule, comprising the steps of:
   (a) absorption labeling a target biological molecule in a specimen using a colloidal silica particle containing at least one kind of light absorbing member selected from the group consisting of DY590, DY495, DY415, Alexa Fluor405, Alexa Fluor488 and Alexa Fluor568, and then performing a molecular recognition between a first recognition substance fixed on a plate and the target biological molecule absorption labeled by using the colloidal silica particle; and
   (b) detecting or quantifying an absorption of the colloidal silica particle on a plate.

4. A method for detection or quantification of a biological molecule, comprising the steps of:
   (a) performing a molecular recognition between a first recognition substance fixed on a plate and a target biological molecule in a specimen;
   (b) performing a molecular recognition between a second recognition substance and the target biological molecule after molecular recognized with the first recognition substance;
   (c) performing a molecular recognition of the second recognition substance by using a colloidal silica particle containing at least one kind of light absorbing member selected from the group consisting of DY590, DY495, DY415, Alexa Fluor405, Alexa Fluor488 and Alexa Fluor568 having a third recognition substance attached to a surface thereof; and
   (d) detecting or quantifying an absorption of the colloidal silica particle on the plate.

5. A method for detection or quantification of a biological molecule, comprising the steps of:
   (a) performing a molecular recognition between a first recognition substance fixed on a plate and a target biological molecule in a specimen;
   (b) performing a molecular recognition between a second recognition substance and the target biological molecule after molecular recognized with the first recognition substance;
   (c) performing a molecular recognition of the second recognition substance using a third recognition substance;
   (d) performing a molecular recognition of the third recognition substance using a colloidal silica particle containing at least one kind of light absorbing member selected from the group consisting of DY590, DY495, DY415, Alexa Fluor405, Alexa Fluor488 and Alexa Fluor568 having a fourth recognition substance attached to a surface thereof; and
   (e) detecting or quantifying an absorption of the colloidal silica particle on the plate.

6. The method for detection or quantification of the biological molecule according to claim 1, wherein the target biological molecule is an antigen, an antibody, a DNA, an RNA, a saccharide, a sugar chain, a ligand, an acceptor, an avidin, a streptavidin, a biotin, a peptide, or a chemical substance.

7. The method for detection or quantification of the biological molecule according to claim 2, wherein the target biological molecule is an antigen, an antibody, a DNA, an RNA, a saccharide, a sugar chain, a ligand, an acceptor, an avidin, a streptavidin, a biotin, a peptide, or a chemical substance.

8. The method for detection or quantification of the biological molecule according to claim 1, wherein a mean particle diameter of the colloidal silica particles is between 50 nm and 2000 nm.

9. The method for detection or quantification of the biological molecule according to claim 2, wherein a mean particle diameter of the colloidal silica particles is between 50 nm and 2000 nm.

10. The method for detection or quantification of the biological molecule according to claim 1, wherein an absorption maximum wavelength regarding the absorption spectrum of the colloidal silica particle is in a range of between 200 nm and 800 nm.

11. The method for detection or quantification of the biological molecule according to claim 2, wherein an absorption maximum wavelength regarding the absorption spectrum of the colloidal silica particle is in a range of between 200 nm and 800 nm.

12. The method for detection or quantification of the biological molecule according to claim 10, wherein a molar absorption coefficient of the colloidal silica particle regarding a maximal wavelength of the absorption spectrum is not less than $5 \times 10^7 \, M^{-1} cm^{-1}$.

13. The method for detection or quantification of the biological molecule according to claim 11, wherein a molar absorption coefficient of the colloidal silica particle regarding a maximal wavelength of the absorption spectrum is not less than $5 \times 10^7 \, M^{-1} cm^{-1}$.

14. The method for detection or quantification of the biological molecule according to claim 1, wherein the colloidal silica particles containing the light-absorbing substance individually contains one to four types of light-absorbing substances having a different maximal wavelength therebetween in the absorption spectrum respectively.

15. The method for detection or quantification of the biological molecule according to claim 2, wherein the colloidal silica particles containing the light-absorbing substance individually contains one to four types of light-absorbing substances having a different maximal wavelength therebetween in the absorption spectrum respectively.

* * * * *